US005366874A

United States Patent [19]

Eidels et al.

[11] Patent Number: 5,366,874

[45] Date of Patent: Nov. 22, 1994

[54] MOLECULAR CLONING AND EXPRESSION OF BIOLOGICALLY-ACTIVE DIPHTHERIA TOXIN RECEPTOR

[75] Inventors: Leon Eidels, Dallas, Tex.; Joseph G. Naglich, Lawrenceville, N.J.; James E. Metherall, Salt Lake City, Utah

[73] Assignee: Board of Regents, The University of Texas System, Austin, Tex.

[21] Appl. No.: 935,309

[22] Filed: Aug. 24, 1992

Related U.S. Application Data

[63] Continuation-in-part of Ser. No. 899,071, Jun. 12, 1992, which is a continuation-in-part of Ser. No. 816,701, Jan. 2, 1992, abandoned.

[51] Int. Cl.[5] .......... C12N 15/12

[52] U.S. Cl. .......... 435/69.1; 435/7.1; 435/7.2; 435/252.3; 435/320.1; 536/23.5

[58] Field of Search .......... 435/69.1, 252.3, 320.1; 436/501

[56] References Cited

U.S. PATENT DOCUMENTS 4,675,285 1/1987 Clark et al. .......... 435/172.3

OTHER PUBLICATIONS

Cieplak, Witold, et al., "Diphtheria Toxin Receptor, Identification of Specific Diphtheria Toxin-Binding Proteins on the Surface of Vero and SB-C-1 Cells," *The Journal of Biological Chemistry,* 262(27):13245-13253, 1987.

Higashiyama, Shigeki, et al., "A Heparin-Binding Growth Factor Secreted by Macrophage-Like Cells That is Related to EGF," *Science,* 251:936-939, 1991.

Higashiyama, Shigeki, et al., "Structure of Heparin--Binding EGF-like Growth Factor: Multiple Forms Primary Structure and Glycosylation of the Mature Protein," *The Journal of Biological Chemistry,* 267(9):6205-6212, 1992.

Madshus, Inger Helene, et al., "Membrane Translocation of Diphtheria Toxin Carrying Passenger Protein Domains," *Infection and Immunity,* 60(8):3296-3302, 1992.

Mitamura, Toshihide, et al., "The 27-kD Diphtheria Toxin Receptor-Associated Protein (DRAP27) from Vero Cells is the Monkey Homologue of Human CD9 Antigen: Expression of DRAP27 Elevates the Number of Diphtheria Toxin Receptors on Toxin-Sensitive Cells," *The Journal of Cell Biology,* 118(6):1389-1399, 1992.

Naglich, J. G., et al., "Expression of Functional Diphtheria Toxin Receptors on Highly Toxin-Sensitive (List continued on next page.)

*Primary Examiner*—Robert J. Hill, Jr.
*Assistant Examiner*—John D. Ulm
*Attorney, Agent, or Firm*—Arnold, White & Durkee

[57] ABSTRACT

DT-resistant wild-type mouse L-M cells were co-transfected with a cDNA library constructed from RNA of highly toxin-sensitive monkey Vero cells and with a neomycin resistance gene. One DT-sensitive ($DT^S$) colony was isolated from 8,000 stably-transfected neomycin-resistant L-M colonies screened by replica plate assays. The purified $DT^S$ mouse cells are highly toxin-sensitive (~1,000-fold more so than L-M cells and only ~10-fold less than Vero cells) and are protected from DT toxicity on incubation with a nontoxic competitive DT inhibitor (CRM 197). Importantly, the cell surface receptors on $DT^S$ cells specifically bind radioiodinated DT, which is inhibited by unlabelled DT and the DT receptor-binding domain (HA6DT). A plasmid conferring DT-sensitivity (pDTS) was rescued from $DT^S$ cells, and the screening procedure repeated until a single cDNA encoding the DT receptor was isolated. The cDNA is predicted to encode an integral membrane protein that corresponds to the precursor of a human heparin-binding EGF-like growth factor. The DT sensitivity protein is thus a growth factor precursor which is exploited by DT, thus allowing the toxin to enter the cell.

3 Claims, 8 Drawing Sheets

OTHER PUBLICATIONS

Mouse Cells That Specifically Bind Radioiodinated Toxin," *Proceedings of the National Academy of Science,* 89:2170–2174, 1992.
Naglich, Joseph G. and Leon Eidels, "Isolation of Diphtheria Toxin–Sensitive Mouse Cells from a Toxin–Resistant Population Transfected with Monkey DNA," *Proceedings of the National Academy of Science,* 87:7250–7254, 1990.
Naglich, J. G., et al., "Expression Cloning of a Diphtheria Toxin Receptor: Identity with a Heparin–Binding EGF–like Growth Factor Precursor," *Cell,* 69:1051–1061, 1992.
Naglich, J. D., et al., "Expression Cloning of the Diphtheria Toxin Receptor Gene," *Joint Meeting of 1992 ASBMB/Biophysical Society,* Houston, Tex., Feb. 9–13, 1992, Published in FASEB Journal, 6(1), A262, 1992. Abstracts only.
Prior, T. I., et al., "Barnase Toxin: A New Chimeric Toxin Composed Pseudomonas Exotoxin A and Barnase," *Cell,* 64:1017–1023, 1991.
Stenmark, H., et al., "Peptides Fused to the Amino–Terminal End of Diphtheria Toxin are Translocated to the Cytosol," *Journal of Cell Biology,* 113(5):1025–1032, 1991.
Guidi–Rontani, Chantal, "Cytotoxic Activity of a Recombinant Chimaeric Protein between *Pseudomonas aeruginosa* Exotoxin A and *Corynebacterium diphtheriae* Diphtheria Toxin," *Molecular Microbiology,* 6(10):1281–1287, 1992.
Cell, Reg. 1:811–19 (Oct. 1990) Besher et al. Isolation and Characterization of a MacPlage derived Heparin–Biulding Growth Factor.
Nature 311:626–631 (18 Apr. 1984) Leonard et al. Molecular Cloning and Expression of CDN for the Human Inteleckin–2 Receptor.
Nature 313:806–810 (28 Feb. 1985) Jacogs et al. Isolation and Characterization of Growth and CPNA Clove of Human Ertyhroyoietin.

```
     5'   CTCTAAAGGCCGCTTCGAAAGTGACTGGTGCCTCGCCGCCTCCTCTCGGTGCGGGACC     58

     ATGAAGCTGCTGCCGTCGGTGGTGCTGAAGCTCCTTCTGGCTGCAGTTCTTTCGGCACTGGTGACTGGCGAGAGCCTGGAGCAGCTTCGG   148
1    MetlysleuLeuProSerValValLeuLysLeuLeuLeuAlaAlaValLeuSerAlaLeuValThrGlyGluSerLeuGluGlnLeuArg
                                    Phe                                                 Arg

     AGAGGGCTAGCTGCTGGAACCAGCAACCCGGACCCTTCCACTGGATCTACGGACCAGCTGCTACGCCTAGGAGGCGGCCGGGACCGGAAA   238
31   ArgGlyLeuAlaAlaGlyThrSerAsnProAspProSerThrGlySerThrAspGlnLeuLeuArgLeuGlyGlyGlyArgAspArgLys
                                      Pro   Val                   Pro

     GTCCGTGACTTGCAAGAGGCAGATCTGGACCTTTTGAGAGTCACTTTATCCTCCAAGCCACAAGCACTGGCCACACCAAGCAAGGAGGAG   328
61   ValArgAspLeuGlnGluAlaAspLeuAspLeuLeuArgValThrLeuSerSerLysProGlnAlaLeuAlaThrProSerLysGluGlu
                                                                                  Asn

     CACGGGAAAAGAAAGAAGAAAGGCAAGGGACTAGGGAAGAAGAGGGACCCATGTCTTCGGAAATACAAGGACTTCTGCATCCACGGAGAA   418
91   HisGlyLysArgLysLysLysGlyLysGlyLeuGlyLysLysArgAspProCysLeuArgLysTyrLysAspPheCysIleHisGlyGlu

     TGCAAATATGTGAAGGAGCTCCGGGCTCCCTCCTGCATCTGCCACCCAGGTTACCATGGAGAGAGGTGTCATGGGCTGAGCCTCCCAGTG   508
121  CysLysTyrValLysGluLeuArgAlaProSerCysIleCysHisProGlyTyrHisGlyGluArgCysHisGlyLeuSerLeuProVal

     CAAAATCGCTTATATACCTATGACCATACAACTATCCTGGCTGTGGTGGCCGTGGTGCTGTCCTCTGTCTGTCTGCTGGTCATCGTGGGG   598
151  GluAsnArgLeuTyrThrTyrAspHisThrThrIleLeuAlaValValAlaValValLeuSerSerValCysLeuLeuValIleValGly

     CTTCTCATGTTTAGGTACCATAGGAGAGGTGGTTATGATGTGGAAAACGAAGAGAAAGTGAAGTTGGGCATGACTAATTCCCACTGAGAG   688
181  LeuLeuMetPheArgTyrHisArgArgGlyGlyTyrAspValGluAsnGluGluLysValLysLeuGlyMetThrAsnSerHisEnd

     AGACTTGTGCTCAAGGAATCAGCTGGTGACTGCTACCTCTGAGAAGACACAAGGTGATTTCAGACTCCAGAGGGGAAAGACGTCACATCT   778

     AGCCACAAAGACTCCTTCATCCCCAGTCGCCATCTAGGATTGGGCCTCCCATAATTGCTTTGCCAAAATACCAGAGCCTTCAAGTGCCAA   868

     ACCGAGTATGTCTGATGGTATCTGGGTGAGAAGAAAGCAAAAGCAAGGGACCTTCATGCCCTTCTGATTCCCCTCCACCAAGCCCCACTT   958

     CCCCTTATAAGTTTGTTTAAGCACTTACTTCTGGATTAGAATGCCGGTTAAATTCCATATGCTCCAGGATCTTTGACTGAAGAAAAAAAA   1048

     AAAAAAAAAAAAAAA    3'                                                                         1063
```

FIGURE 7

MOLECULAR CLONING AND EXPRESSION OF BIOLOGICALLY-ACTIVE DIPHTHERIA TOXIN RECEPTOR

The government owns certain rights in the present invention pursuant to NIH grant number AI-16805.

The present application is a continuation-in-part of U.S. Ser. No. 07/899,071, filed Jun. 12, 1992, which was a continuation-in-part of U.S. Ser. No. 07/816,701, filed Jan. 2, 1992, now abandoned.

BACKGROUND OF THE INVENTION

1. Field of the Invention

The present invention relates generally to the use of molecular biological techniques in the cloning, identification and characterization of a mammalian diphtheria toxin (DT) receptor. In particular, the invention relates to DNA segments and recombinant vectors encoding a DT receptor, to the expression of the biologically active DT receptor in recombinant cells, to methods for conferring DT sensitivity to a cell, and to methods for the identification of candidate substances that bind to the DT receptor. It is also envisioned that the DT receptor may be of use in the development of novel drug delivery systems, and as a negative-selectable marker in gene transfer systems.

2. Description of the Related Art

Diphtheria toxin (DT), a potent exotoxin produced by lysogenized strains of *Corynebacterium diphtheriae*, is a multifunctional protein that kills susceptible mammalian cells. It is composed of two disulfide-linked protein fragments, both of which are required for the intoxication process (Collier, 1975; Pappenheimer, 1977; Eidels et al., 1983; Middlebrook & Dorland, 1984). The A-fragment catalyzes the ADP-ribosylation of eukaryotic elongation factor 2, thereby inhibiting protein synthesis. The B-fragment is responsible for binding of the toxin to cells and is essential for facilitating the entry of the A-fragment into the cytosol (Collier, 1975; Pappenheimer, 1977; Eidels et al., 1983; Middlebrook & Dorland, 1984).

The existence of specific cell-surface DT receptors was first demonstrated by Ittelson & Gill (1973) employing a competitive inhibition of binding approach, and it is now known that DT enters susceptible mammalian cells via receptor-mediated endocytosis (Morris et al., 1985; Keen et al., 1982). The initial step involves the binding of DT to a specific cell-surface receptor, followed by internalization of the toxin:receptor complexes into coated pits and translocation of the A-fragment into the cytosol. Not all mammalian cells are equally sensitive to DT (Middlebrook & Dorland, 1977b; Middlebrook et al., 1978). For example, monkey kidney cells such as Vero cells, are highly sensitive, whereas human and hamster cells are moderately sensitive and mouse and rat cells are resistant.

As elongation factor 2 of all mammalian cells can be ADP-ribosylated by the DT A-fragment, it is generally believed that the difference in sensitivity to DT between species is due to the number of functional cell-surface DT receptors. In this regard, Vero cells display $1-2\times10^5$ receptors per cell (Middlebrook et al., 1978), whereas mouse and rat cells lack detectable receptors (Eidels et al., 1983; Stenmark et al., 1988). Prior to the present invention, a specific DT receptor has not been completely isolated or characterized, although a 27 kD DT receptor-associated Vero cell protein has recently been reported (Iwamoto et al., 1991).

The present inventors recently isolated and characterized a diphtheria toxin-sensitive ($DT^S$) mouse cell line obtained by transfection of mouse L-M cells with monkey cell genomic DNA. A replica plate screening procedure was developed and employed to detect and isolate mouse cells that had acquired DT sensitivity (Naglich & Eidels, 1990). The degree of toxin sensitivity of the $DT^S$ mouse cells in this study was only moderate and no specific binding of radioiodinated DT to the cell surface was detected. Although the mode of action of DT after it enters a cell is generally known, prior to the studies disclosed herein, there existed a marked lack of knowledge concerning the DT receptor molecule.

SUMMARY OF THE INVENTION

The present invention addresses these and other shortcomings in the art through the cloning, sequencing and identification of a mammalian diphtheria toxin (DT) receptor, and its expression in a biologically-active form. The inventors surprisingly found the DT receptor molecule to correspond to a precursor of a heparin-binding EGF-like growth factor (HB-EGF). The invention particularly discloses isolated DNA segments and recombinant vectors encoding a DT receptor, for use as nucleic acid hybridization probes or in the expression of a biologically active receptor in recombinant cells. Also disclosed are methods for conferring DT sensitivity to a cell, and methods for use in the identification of candidate substances that bind to the DT receptor. The DT receptor is proposed to be of use as a negative-selectable marker in gene transfer protocols and in the development of novel drug delivery systems.

As used herein, the term "DNA segment" is intended to refer to a DNA molecule which has been isolated free of total genomic DNA of a particular species. Therefore, a DNA segment encoding a DT receptor is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phage, viruses, and the like.

In certain embodiments, the invention concerns isolated DNA segments and recombinant vectors incorporating DNA sequences which encode a DT receptor that includes within its amino acid sequence the amino acid sequence of SEQ ID NO:2, corresponding to the monkey kidney (VERO) cell DT receptor. The inventors demonstrate herein that this DT receptor sequence surprisingly corresponds to the sequence of a precursor of a heparin-binding EGF-like growth factor (HB-EGF) (Higashiyama et al., 1991; 1992). Recombinant vectors and isolated segments may variously include the DT receptor coding regions itself, coding regions bearing selected alterations or modifications in the basic coding region or may encode larger polypeptides which nevertheless include sequences which will confer DT sensitivity when expressed in a previously DT resistant cell.

However, it will be understood that this aspect of the invention is not limited to the particular DNA and amino acid sequences of SEQ ID NO:1 and SEQ ID NO:2, respectively. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and their encoded proteins. Alternatively, functionally equivalent proteins or peptides may be created via the application of recombinant DNA technology, in which changes in the protein structure may be engineered, based on considerations of the properties of specific amino acids being exchanged.

As such, modifications and changes may be made in the structure of the DT receptor and still obtain a molecule having similar or otherwise desirable characteristics. For example, certain amino acids may be substituted for other amino acids in a protein structure without appreciable loss of interactive binding capacity with structures such as, for example, ligand-binding sites or antibody-binding regions. Since it is the interactive capacity and nature of a protein that defines that protein's biological function, certain amino acid sequence substitutions can be made in a protein sequence (or, of course, its underlying DNA coding sequence) that result in a protein with similar or even countervailing properties (e.g., antagonistic v. agonistic). Therefore, it is contemplated by the inventors that various changes may be made in the sequence of the peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982; incorporated herein by reference). It is known that certain amino acids may be substituted for other amino acids having a similar hydropathic index or score and still retain a similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules such as ligands and substrates. In making conservative changes based upon the hydropathic index, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101 teaches that the greatest local average hydrophilicity of a protein, as governed by the hydrophilicity of its adjacent amino acids, correlates with its inmunogenicity and antigenicity, i.e. with a biological property of the protein.

As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); (0±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In certain embodiments, the present invention concerns the molecular cloning of a DT receptor, preferably from highly DT sensitive cells. The term "highly DT sensitive cells" refers to cells such as monkey kidney cells that are very susceptible to diphtheria toxicity and that express a high number of DT receptors, for example, on the order of 1–2×$10^5$ receptors per cell. Presumably, these cells active transcribe the DT receptor gene into specific mRNA and efficiently translate the mRNA to produce high numbers of DT receptor molecules. Accordingly, certain advantages are evident in employing such highly toxin-sensitive cells in the creation of a cDNA library from which a DT receptor cDNA could be isolated.

To create a cDNA library one would first obtain total RNA from a cell source expressing the DT receptor and use it as a template for the synthesis of cDNA using the enzyme reverse transcriptase (Sambrook et al., 1989). As stated above, one may prefer to employ highly DT sensitive cells, such as Vero cells, as a source of RNA. However, it is contemplated that any cell type expressing a DT receptor, in particular, a cell of human origin, could be employed as a source of RNA for constructing a cDNA library. As cells expressing functional receptors will be sensitive to DT, a method of identifying a suitable DT-expressing cell type for use in such embodiments, such as a human cell, would be to simply determine whether the cell is sensitive to DT.

The cDNA molecules created by reverse transcription would then be size-fractionated (preferably to a size of on the order of ≧1 kb) and ligated into a suitable plasmid vector (such as pcDNA1, pSV2, pRc RSV, or the like) using appropriate oligonucleotide linkers and restriction enzyme technology (Sambrook et al., 1989). The ligated material would then be used to transform competent host cells, such as *E. coli* MC 1061/P3 cells, to yield a cDNA library. This library or portions of this library could be amplified following plasmid isolation and DNA could be purified using the alkaline lysis and cesium chloride protocols, respectively (Sambrook et al., 1989).

The cloning strategy employed by the present inventors involved co-transfecting DT resistant cells with a selectable marker and a cDNA library constructed from highly toxin-sensitive cells. The DT resistant cells chosen by the present inventors were wild-type mouse L-M cells, because they are resistant to DT and lack detectable DT receptors, they are easily transfected using available protocols and because they replicate at a rate that is convenient for experimental manipulation. However, it is contemplated that other naturally-occurring DT resistant cells, such as 3T3 cells, or NRK cells, and the like, may be used, and also any experimentally created DT receptor-deficient cell. The second selectable marker employed by the inventors was the neomycin resistance gene. By subsequently exposing the cells to a selective agent, in this case Geneticin (G418, a neomycin derivative), one can first select for those cells that have incorporated foreign DNA, since only such cells can survive under these conditions. It will be appreciated that many selectable markers would be suitable for use in this manner, such as thymidine kinase (TK), hyg B, gpt, and the like.

Stably-transfected colonies, in this case, neomycin-resistant ($Neo^R$) L-M colonies, can then be screened for DT sensitivity, for example, using the replica plating protocol disclosed herein. In such embodiments, transfected colonies are overlaid with a stack of three filter membranes, such as polyester-PeCap HD7-17 membranes, and a layer of glass beads and allowed to grow through the filter membrane stack. The stack of filters is then removed, and the bottom filter incubated with an appropriate amount of DT, such as 2 $\mu$g DT/ml, for 18 hours at 37° C. The DT-treated $Neo^R$ colonies are then washed with a buffer such as PBS/Ca/Mg, and assayed for the degree of DT resistance.

As DT specifically inhibits protein synthesis, a particularly suitable method for assaying DT sensitivity is to determine the ability of the cells to incorporate a labelled amino acid, such as [$^{35}$S]-L-methionine, or [$^3$H]leucine, into protein. As such, the macromolecules of the cells are precipitated, for example using ice-cold 15% (w/v) trichloroacetic acid (TCA), treated with 1M sodium salicylate (pH 6.25) solution, dried in a vacuum oven at ~80° C., and finally subjected to fluorography, by exposing to XAR-5 film for ~16 hours at −80° C., for example. The colonies on the DT-treated filters are then stained with a protein dye such as Coomassie G-250 and the stained colonies compared to the corresponding areas on the fluorogram. Those colonies which stained blue on the filter but appeared as a clear zone on the fluorogram, i.e. were not able to incorporate a radiolabel and thus not able to conduct protein synthesis. Viable cells representing these colonies were isolated by cutting out the corresponding individual colonies from the middle membrane filter.

Southern analysis of the $DT^S$ cDNA transfectant cells revealed that they contained several different copies of vector sequences. Several strategies exist for recovering and isolating specific cDNAs from eukaryotic cells (Littman et al., 1985, Weiland et al., 1990). The approach taken by the present inventors to isolate (rescue) the specific cDNA responsible for DT sensitivity takes advantage of the components of the eukaryotic expression vector employed.

The chosen vector, pcDNA 1, contains a SV40 origin of replication which allows for specific replication of vector-containing sequences in cells that produce large T antigen such as COS cells. The $DT^S$ cDNA-containing L cells can be fused with COS cells using PEG and conventional tissue culture techniques, as will be known to those of skill in the art in light of the present disclosure. The presence of large T antigen in the hybrid cells results in amplification of the vector/cDNA sequences. Low molecular weight DNA (i.e. vector/DNA) can then be isolated, for example, using a Hirt cell lysate procedure (1967), and used to transform competent *E. coli* cells. The recombinant *E. coli* transformants can then be screened, preferably by Southern analysis employing a radiolabeled CMV DNA probe. Cells from colonies that hybridized to the CMV cDNA probe should be pooled into conveniently-sized groups for further analysis.

Plasmids from these pools may then be isolated, purified, and used to co-transfect L cells in the usual fashion. The $Neo^R$ L cells may then be screened for DT sensitivity, using the replica plate assay, when pool(s) generating $DT^S$ mouse cells can be identified. The *E. coli* cells originally used to prepare the chosen positive pool can be subdivided into smaller pools, and the plasmids prepared and retested by co-transfection of L cells and replica plate screening. In this fashion, an individual *E. coli* colony containing a single cDNA responsible for DT sensitivity may be identified. To confirm that this contains the DT sensitivity gene, plasmid DNA (cloned cDNA) may be purified from the chosen positive *E. coli* colony and used in further co-transfection and replica screening assays.

However, it will be appreciated that the present invention is not limited to cloning of the DT receptor from highly DT sensitive cells, nor to the use of the above-described method. It is believed that those of skill in the art of molecular and cellular biology will now, in light of the present disclosure, be able to clone any mammalian, or indeed human, DT receptor, including those from moderate or low DT sensitivity cell types.

In such embodiments, one will be able to screen any DNA library using nucleic acid hybridization probes and/or primers based on the DNA sequence disclosed herein, SEQ ID NO:1, and variations thereof, or sequences that are complementary to those shown in SEQ ID NO:1. Suitable nucleic acid hybridization procedures are well known in the art, for example, see Sambrook et al., (1989), incorporated herein by reference, and are discussed more fully below. Importantly, it should be noted that hybridization probe(s) based upon the sequences of the present invention can be used to screen genomic libraries in addition to cDNA libraries, as discussed above.

As mentioned above, at various stages of the cloning procedure, DNA segments are transfected into DT resistant cells, and the cells subsequently examined for the appearance of a DT sensitive phenotype. Certain aspects of the present invention therefore involve assaying a previously DT resistant cell for DT sensitivity. It is envisioned that this procedure will also find utility in embodiments other than in the cloning of a DT receptor from any source, for example, in structure/function analyses of the DT receptor and mutant or variants thereof, in examining the kinetics of ligand binding and receptor-mediated endocytosis (RME), and the like.

The terms "DT sensitive" and "DT insensitive"/"DT resistant" simply refer to cell types that are, respectively, subject to, and not subject to, the toxic effects of DT when it is added extracellularly. As the toxin needs to be transported into the cell via the specific DT receptor, the terms DT sensitive and DT insensitive also convey information as to the numbers of membrane-bound DT receptors, and/or the affinity of such receptors for the toxin. Assaying for the "appearance of a DT sensitive phenotype" refers to the process of determining whether previously DT insensitive cells become sensitive to extracellular DT, when transfected with a DNA segment. Naturally, the appearance of a DT sensitive phenotype indicates the presence of biologically functional DT receptors at the cell surface. Likewise, a moderately DT sensitive cell can be rendered highly DT sensitive by transformation with DT receptor DNA.

The cytotoxicity assay preferred by the present inventors is based upon determining the ability of the cell to conduct protein synthesis in the presence and absence of extracellular diphtheria toxin. Protein synthesis may be measured by the degree of incorporation of a labelled amino acid into protein. Convenient amino acids for use in this manner are believed to be methionine and leucine, tagged with a radiolabel to create, for example, [$^{35}$S]methionine and [$^{3}$H]leucine.

To conduct a cytotoxicity assay in accordance with the present invention, one would first grow the parent and transformed cells to confluency in a suitable culture medium, such as Dulbeco's Modified Eagle's medium (DMEM), 10% fetal calf serum (FCS). One would then add a buffer such as 20 mM Hepes, pH 7.4, containing varying amounts of DT to the cell monolayers, incubate at 37° C., wash the monolayers to remove unbound DT, for example with PBS/Ca/Mg, and incubate for a further hour in medium which is deficient in a certain amino acid. The cells are then incubated with a radiolabeled form of this amino acid for a final hour, washed, lysed, and assayed for radiolabel incorporation into TCA-precipitable material, i.e. protein. Comparing the values for the parent and transformed cells enables the degree of DT sensitivity acquired by the transformed cell to be determined.

However, it is contemplated that DT toxicity could be assessed by other methods such as the actual cell-killing as assayed by detachment of dead cells from a cell monolayer and quantifying the number of attached cells remaining (Middlebrook & Dorland, 1977a).

DNA segments prepared in accordance with the present invention are proposed to be of use in a variety of applications. For example, in the recombinant production of the DT receptor, or in the expression of the DT receptor in recombinant cells to create novel DT sensitive cells. Additionally, the DT receptor-encoding DNA segments of the present invention can also be used in the preparation of nucleic acid probes or primers, which can, for example, be used in the identification of related gene sequences or in the study of subunit(s) expression, and the like.

Turning firstly to the expression of the DT receptor. Following the cloning of the receptor, one may proceed to prepare an expression system for the recombinant preparation of the receptor, or the creation of a DT sensitive cell. The engineering of the DT receptor gene for expression in a prokaryotic or eukaryotic system may be performed by techniques generally known to those of skill in recombinant expression.

It is believed that virtually any expression system may be employed in the expression of the DT receptor. It is envisioned that even bacterial expression systems may be employed, for example, where one wishes to produce large amounts of the receptor for uses where its functional properties are not of prime importance, such as in the generation of anti-receptor antibodies by immunizing an experimental animal. Of course, where a biologically active receptor is needed, one will prefer to employ a eukaryotic expression system, and most preferably, to use a eukaryotic cell that was previously insensitive to DT, by virtue of lacking the DT receptor.

It is believed that almost any eukaryotic expression system may be utilized for the expression of the DT receptor, for example, baculovirus-based, glutamine synthase-based or dihydrofolate reductase-based systems could be employed.

In any event, to achieve expression of the DT receptor, one would position the coding sequences adjacent to and under the control of a suitable promoter. It is generally understood in the art that to bring a coding sequence under the control of such a promoter, all that is required to position the promotor upstream of (5′ to) the initiator methionine codon that defines the 5′ end of the protein coding region. Typically the initiator methionine codon is the first methionine codon 3′ to, and is within 50 nucleotides of, the transcription initiating site provided by the promoter.

Where eukaryotic expression is contemplated, one will also typically desire to incorporate into the DT transcriptional unit an appropriate polyadenylation site (e.g., 5′-AATAAA-3′) if one was not contained within the original cloned segment. Typically, the poly A addition site is placed about 30 to 2000 nucleotides "downstream" of the terminator codon that defines the 3′ end of the protein coding region.

It is contemplated that virtually any of the commonly employed eukaryotic host cells can be used for expression of the DT receptor. Examples include cell lines typically employed for eukaryotic expression such as 293, AtT-20, HepG2, Vero, HeLa, CHO, WI 38, BHK, COS-7, RIN and MDCK cell lines. In preferred embodiments, the cells used for the expression of the DT receptor will originally be DT insensitive, such as the mouse cell line, L-M, chosen by the inventors.

The DNA sequences disclosed herein will also find utility for generating probes or primers used in nucleic acid hybridization embodiments. As such, it is contemplated that oligonucleotide fragments corresponding to the sequences of seq id no:1 for stretches of between about 10 nucleotides to about 30 nucleotides will find utility. The ability of such nucleic acid probes to specifically to hybridize DT receptor-encoding sequences will enable them to be of use in a variety of embodiments. Importantly, the probes can be used for the cloning of DT receptors, and other related genes from a DT receptor family, from other cell types and mammalian species, and in the detection of complementary sequences in a given sample, such as in Southern and Northern blotting to detect related DNA and RNA, respectively. Nucleic acid segments may also be used in the preparation of mutant species primers, or primers for use in preparing other genetic constructions.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of DT receptor genes or cDNAs. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and or high temperature conditions, such as provided by 0.02M–g0.15M NaCl at temperatures of 50° C. to 70° C. These conditions are particularly selective, and tolerate little, if any, mismatch between the probe and the template or target strand. For example, they are particularly suitable for examining the expression of the same gene in different tissues.

Of course, for some applications, for example, where one desires to prepare mutants employing a mutant primer strand hybridized to an underlying template or where one seeks to isolate DT receptor-encoding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Further embodiments of the present invention concern methods for the expression of a DT receptor in a cell, and methods for conferring DT sensitivity to a cell. To express a DT receptor in a cell, one would prepare a recombinant expression vector bearing the DT receptor DNA, transform a host cell with said recombinant expression vector, and culture the transformed host cell. Similarly, to confer DT sensitivity to a cell in accordance with the present invention, one would express the DT receptor in a host cell, as described above, and subsequently add extracellular diphtheria toxin.

It is contemplated that both cell types that were originally completely insensitive to DT, and cell types that were originally slightly or moderately sensitive to DT will be suitable as targets for DT receptor expression. As such, the term "conferring DT sensitivity to a cell" also includes a situation wherein the DT sensitivity of a host cell is increased by a detectable amount over the untreated parent cells, when transformed with DT receptor-encoding DNA.

Related embodiments concern a method for assaying the effects of diphtheria toxin in a cell which has been rendered DT sensitive, preferably by conducting a cytotoxicity assay, as described above. Accordingly, one would determine the level of protein synthesis that transformed cell is able to support, for example by measuring the incorporation of a labelled amino acid into protein. In aspects where the host cell was sensitive to DT prior to transformation with the DT receptor, one would conduct parallel assays and determine the difference between the transformed and untransformed cells. Such parallel assays may also form the basis of mutational analyses, wherein the effects of specific alterations in the DT receptor structure could be examined, and their effects compared to the native receptor.

In still further methodological embodiments, the invention concerns a method for identifying compounds which bind to the DT receptor, herein termed "candidate substances". It is contemplated that this screening technique will prove useful in the general identification of any compound that will bind to the DT receptor. Furthermore, this method can be used for the identification of the natural biological ligand(s) of the DT receptor. Of course, the entry of diphtheria toxin into mammalian cells via the receptor represents an exploitation of the protein, and not its true function.

The inventors have recently shown that the DT receptor corresponds to a precursor of a heparin-binding EGF-like growth factor (HB-EGF), known to be secreted by macrophage-like cells (Higashiyama et al., 1991; 1992). Secreted HB-EGF has been shown to be a potent mitogen and to trigger autophosphorylation of the EGF receptor (Higashiyama et al., 1991; 1992). However, the biological properties and functions of this molecule as an integral cell membrane protein have not been addressed. It may function as a cell-surface receptor for a natural ligand which triggers or modulates essential biological process(es). It is therefore reasonable to assume that cells that are resistant to DT may express a homologue of the DT receptor that functions in this natural process but fails to bind and/or internalize DT due to natural amino acid variations.

It is anticipated that through the use of the DNA hybridization protocols described above, DNA clones for the DT receptor homologues could be isolated. Furthermore, the inventors contemplate that although these homologues fail to bind DT, they can be considered natural variants of the DT receptor, not only based on sequence similarity but also with regard to their true biological function.

The method for identifying candidate substances which bind to the cell surface DT receptor is based on a competitive binding assay employing radiolabeled DT. To carry out an assay of this sort, one would prepare a recombinant host cell that expressed a biologically active DT receptor, grow the cells until confluent and then place the monolayers on ice and wash with an ice-cold buffer, such as PBS/Ca/Mg. One would then incubate at 4° C. for approximately five hours in media to promote binding, such as Medium 199, 20 mM Hepes, 50 μg/ml bovine serum albumin (BSA), 100 μg/ml gelatin, pH 7.4, containing a mixture of radiolabeled DT, such as a radioiodinated form, and a candidate substance, or a mixture of candidate substances. The tendency would be for the radiolabeled DT to bind to the DT receptor, unless it was displaced by a candidate substance. One would then remove any unbound diphtheria toxin and candidate substance(s) by washing, for example with PBS/Ca/Mg, solubilize the cells with a solution such as 0.2N NaOH, and measure the cell-associated radioactivity.

A positive control in a binding assay of this sort would be the amount of cell-associated radioactivity when the cells were incubated with radiolabeled DT alone. In contrast, a negative control would be the amount of cell-associated radioactivity when the cells were incubated with a 200-fold excess of unlabeled DT. The presence of a candidate substance that binds to the DT receptor would be indicated by a reduction in the cell-associated radioactivity below the positive control levels, following the simultaneous incubation of the candidate substance(s) and the radiolabeled DT with the recombinant cells. Of course, as is generally known to those of skill in the art, one would eliminate the possibility that a reduction in the cell-associated radioactivity was due to non-specific interference by conducting parallel assays employing similar levels of a protein known not to bind to the DT receptor, such as BSA.

A mixture of candidate substances that would be suitable for analysis in this way would include body fluids such as blood, serum, sputum, and urine; media obtained from cultured cells; or growth factors and peptide hormones. One may also analyze polyclonal or monoclonal antibodies directed against the DT receptor using a competitive binding assay as described above.

Further embodiments of the present invention concern methods for selecting cells with targeted gene modifications. In these procedures, specific genomic sequences are modified by introducing cloned and modified DNA sequences, herein termed "targeting sequences", into a cell and selecting or screening for cells that have specifically incorporated the modifications into the genomic analog of the targeting sequence. This allows for the introduction of specific mutations or modifications into genomic sequences and has wide applicability in research, agriculture and potentially in the treatment of genetic diseases. Gene targeting events have been obtained in cultured cell lines as well as in pluripotent embryonic stem cells, although it is envisioned that other cell systems would also be suitable for gene-targeting.

Mouse embryonic stem cells containing specific targeted events can be used to generate chimeric mice that pass the modification onto their offspring. This can be achieved by introducing the modified stem cells into a blastocyst and implanting the blastocyst into pseudopregnant surrogates. The resulting chimeric offspring can be bred to produce mice with the genetically stable modification and subsequent sister/brother matings allows the generation of mice that are homozygous for the desired modification. Although these procedures have been most successfully employed in mice, it is imagined that similar procedures could be employed to generate specific gene modifications in almost any experimentally or agriculturally important mammalian or avian species.

Selection schemes for isolating cells with specific targeted events often utilize dominant negative-selection systems. These systems kill cells that have incorporated the targeting sequences at sites other than at the desired genomic location. When integration events proceed by homologous recombination at the genomic site of interest, sequences flanking the targeting sequence fail to integrate and are lost from the cell. When integration occurs by non-homologous events, the flanking sequences are usually retained. Flanking the targeting sequence with the gene for a dominate negative-selectable marker allows for the elimination of cells into which the targeting sequence has been integrated by a non-homologous event.

For these purposes, the most commonly utilized dominant negative-selection system is the herpes simplex virus (HSV) thymidine kinase gene using either ganciclovir or FIAU as selection agent. However, the utility of these systems is limited by the fact that both selection agents are nucleotide analogues and are known to be mutagenic. Hence, in these systems, extensive breeding is required to assure that the phenotypes observed in the manipulated animals are due to the targeted event and not due to secondary mutations induced by the selection agent. The diphtheria toxin A-fragment gene has also been used as a negative-selection system for isolating targeted events. However, transient expression of toxin from episomal DNA prior to integration may decrease the efficiency with which targeted events are isolated.

The inventors propose that the diphtheria toxin receptor gene of the present invention could be used as a negative-selectable marker for the selection of targeted gene manipulations. The system has the following number of advantages over the aforementioned systems: (1) expression the DT receptor gene produces DT sensitivity to previously insensitive cells; (2) the small size of the gene is compatible with the molecular biological manipulations required for the construction of DNA segments designed to manipulate target sequences; (3) the selection agent (DT) is not known to be mutagenic; and (4) the selection system is conditional, allowing imposition of selection after an initial expression period during which episomal DNA can be lost.

Still further embodiments of the present invention concern the diphtheria toxin receptor protein itself and methods for its preparation. The preferred approach to prepare a diphtheria toxin receptor in accordance herewith is to firstly express a diphtheria toxin receptor in a recombinant host cell, as discussed above, and then to purify the receptor from the host cell. Of course, it will not be necessary to obtain a highly a purified receptor preparation, indeed, any diphtheria toxin receptor preparation in which the receptor is purified relative to its natural state will have utility. The term "purified relative to its natural state", as used herein, refers to a diphtheria toxin receptor protein from which has been removed various non-DT receptor components, and which composition substantially retains its DT binding activity.

Any one of a variety of methods may be employed to purify a diphtheria toxin receptor protein relative to its natural state. For example, one may simply and advantageously fractionate the recombinant host cells and obtain the plasma membrane-containing fraction. Alternatively, the diphtheria toxin receptor protein may be further purified, either from whole or fractionated cells, using any of the techniques generally known to those of skill in the art. These may include, for example, differential solubility under a variety of conditions, pH- or heat-stability, and a wide range of chromatographic techniques which separate proteins based upon properties such as size, charge, hydrophilicity, and the like. Such chromatographic techniques include, for example, gel filtration, anion exchange, cation exchange, and immuno- or affinity-chromatography. During receptor process, it is contemplated that assays, based generally upon DT binding, will be conducted at various intervals.

Further methodological embodiments of the present invention concern the use of the diphtheria toxin receptor protein to bind diphtheria toxin. To use the DT receptor in this manner, it is envisioned that one would contact a composition suspected of containing a diphtheria toxin molecule with the receptor protein under conditions to allow binding of the toxin to the receptor. It is contemplated the diphtheria toxin receptor protein for use in such a method may either be present at the surface of a recombinant host cell, or alternatively, may be in a form purified relative to its natural state.

FIG. 7. Structure of the Monkey Cell cDNA Encoding the DT Sensitivity Protein. Nucleotide sequence of the cDNA encoding the monkey DT sensitivity protein and the predicted amino acid sequence (GenBank accession number M93012). Nucleotide residues are numbered on the right column. Amino acid residues are numbered on the left column; residue 1 is the putative amino-terminal methionine. The single underline indicates the putative signal sequence and the double underline indicates the putative transmembrane region. The amino acid residues indicated below the predicted amino acid sequence of the monkey DT sensitivity protein are those that differ in the human heparin-binding EGF-like growth factor precursor (GenBank accession number M60278). The boxed cysteine residues are conserved among the members of the EGF/TGF-α family.

Figure 8:
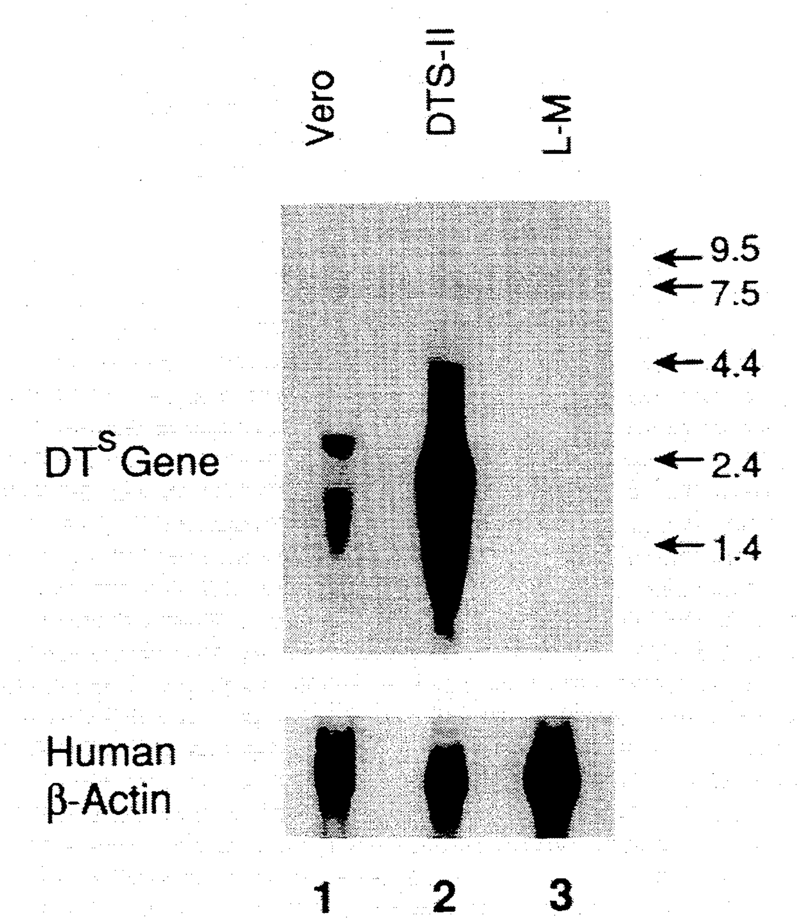

FIG. 8. Northern Blot Analysis of RNA from Vero, $DT^S$-II and L-M Cells. An aliquot of total RNA (25 μg of Vero cell or L-M cell; 18 μg of $DT^S$-II cell) was subjected to electrophoresis and blotted onto a nylon membrane. Hybridization was performed at 42° C. for 20 hours with a mixture of three single-stranded uniformly [$^{32}$P]-labeled cDNA probes corresponding to the entire monkey DT sensitivity gene (each probe $\sim 7\times10^6$ cpm/ml of hybridization solution) or with a single-stranded uniformly [$^{32}$P]-labeled cDNA probe corresponding to the human β-actin gene ($2\times10^6$ cpm/ml of hybridization solution). The filters were washed and exposed to Kodak XAR-5 film with an intensifying screen for 18 hours at −80° C. In both panels, Vero cell RNA (lane 1); $DT^S$-II cell RNA (lane 2); and L-M cell RNA (lane 3). The positions of RNA markers run in an adjacent lane are indicated in the right margin (in kilobases).

DETAILED DESCRIPTION OF THE PREFERRED EMBODIMENTS

DT sensitivity was conferred to L-M cells using either Vero cell genomic DNA or a cDNA expression library prepared from Vero cell mRNA. Using a novel replica plate protocol, transfected L-M cells were isolated that had acquired DT sensitivity. Importantly, no colonies obtained from control co-transfections ever gave rise to a "spontaneous" $DT^S$ colony. Using this system, the inventors isolated and characterized a monkey cell cDNA that confers DT sensitivity when expressed in normally toxin-resistant L-M cells, which lack functional DT receptors. The transfected cells are highly toxin-sensitive and express functional high-affinity DT receptors at the cell surface. These receptor molecules are also trypsin-sensitive and bind CRM 197 competitively with DT.

First analyses of the amino acid sequence encoded by the DT sensitivity gene suggested that the gene encoded a receptor-like, integral membrane protein, as would be consistent for a cell-surface receptor involved in DT binding and intoxication. In fact, the predicted amino acid sequence of the DT receptor was found to correspond to a precursor of a heparin-binding EGF-like growth factor (HB-EGF) (Higashiyama et al., 1991; Higashiyama et al., 1992).

Mature HB-EGF, a member of the EGF-family of growth factors, is a glycoprotein which has been shown to be mitogenic for BALB-3T3 fibroblasts and smooth muscle cells but not endothelial cells (Higashiyama et al., 1991), and which competes with EGF for binding to the EGF receptor (Higashiyama et al., 1992). It has been suggested and in some cases shown that growth factor precursors, as integral plasma membrane proteins, can function in the regulation of cell growth and differentiation as well as in cell-cell interactions (Brachmann et al., 1989; Massague, 1990; Mroczowski et al., 1989; Plowman et al., 1990; Wong et al., 1989).

The results presented herein define a novel and unexpected function for the HB-EGF precursor as a receptor for a bacterial toxin. It seems likely that other proteins and viruses may similarly exploit growth factor precursors as receptors to gain illicit entry into cells.

The following examples illustrate techniques discovered by the inventors for the molecular cloning, sequencing and identification of the diphtheria toxin (DT) receptor, as well as techniques for the conferring DT sensitivity to a cell. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Isolation of a DT Sensitive Recombinant Cell Line

A. Methods

Materials

All tissue culture reagents were obtained from Sigma with the exception of fetal bovine serum which was purchased from Cell Culture Laboratories (Cleveland, Ohio). Geneticin (G418-sulfate) was obtained from GIBCO. $^{125}$I-NaI (IMS 30; 13–17 μCi/μg; 1 $Ci=3.7\times10^{10}$ becquerels), [$^{35}$S]-L-methionine (>800 Ci/mmole), [$^{32}$P]-α-dCTP (3000 Ci/mmole), [$^{35}$S]-α-dATP (≧1000 Ci/mmole) and L-[4,5-$^3$H]-leucine (60 Ci/mmol) were obtained from Amersham. HA6DT was prepared by specific hydroxylamine cleavage of DT and purified as previously described (Rolf et al., 1990). *C. diphtheriae* CRM 197 protein was purchased from the Swiss Serum and Vaccine Institute (Berne, Switzerland). 1,3,4,6-tetrachloro-3α,6α-diphenylglycoluril (Iodogen) was obtained from Pierce. Hepes, calcium chloride, trichloroacetic acid, salicylic acid, and salmon sperm DNA were obtained from Sigma. Urea and DNA restriction enzymes were obtained from Boehringer Mannheim Biochemicals, and reagents for oligonucleotide labeling from Pharmacia. Guanidine thiocyanate was obtained from Curtin Matheson Scientific Inc. Cesium chloride was obtained from Fisher Biochemicals. All other chemicals utilized were of the highest purity available. Polyester-PeCap HD7-17 membranes were purchased from Tetko (Elmsford, N.Y.), and Zeta-Probe nylon membranes and ultrapure agarose, from Bio-Rad.

Diphtheria Toxin

Partially purified DT was purchased from Connaught Laboratories (Ontario, Canada, lot D721) and purified further by anion-exchange chromatography according to published methods (Pappenheimer et al., 1972) with modifications (Cieplak et al., 1987). Limited proteolysis of DT to generate disulfide-linked A and B toxin fragments (nicked toxin) was carried out with trypsin as previously described (Proia et al., 1980). DT was radioiodinated by the Iodogen method as described (Cieplak et al., 1987); typically the labeling procedure resulted in a specific radioactivity of $1-2\times10^7$ cpm/μg of protein.

Cell Culture

Vero (CCL 81), COS7 (CRL1651) and L-M(TK−) (CCL 1.3) cells were obtained from the American Type Culture Collection (Rockford, Md.). Vero and L-M(TK−) cell monolayers were grown in Dulbecco's modified Eagle's medium (DMEM) containing 10% fetal bovine serum at 37° C. in an atmosphere of 5% $CO_2$ in air.

Construction of Monkey cDNA Library

Total RNA was obtained from Vero cells (Sambrook et al., 1989) and cDNA was synthesized under contract with Invitrogen Corp., San Diego, Calif.). Size-fractionated monkey cDNA inserts were ligated into the plasmid vector pcDNA 1 using nonpalindromic BstX1 linkers. The ligated material was then used to transform competent *E. coli* MC 1061/P3 cells yielding a monkey cDNA library of approximately $4.1\times10^6$ independent colonies. A representative portion of this library was amplified 1,000-fold, the plasmids isolated using an alkaline lysis protocol and then purified twice using caesium chloride (Sambrook et al., 1989) before being used to transfect wild-type L-M cells.

Isolation of Plasmid and Genomic DNA

Monkey cell cDNA in the pcDNA1 vector, DNA from plasmids pSV2-neo [American Type Culture Collection (Rockford, Md.)] and plink760 (Thomsen et al., 1984) was extracted from *E. coli* DH5α using an alkaline lysis protocol and purified twice using caesium chloride. Mouse genomic DNA was obtained from cells utilizing an Applied Biosystems 340A Nucleic Acid Extractor (Foster City, Calif.).

Cotransfection with Monkey Cell-Derived cDNA and neo DNA

Mouse L-M cells ($5\times10^5$ per 100×15 mm dish) were transfected with a mixture of 5 μg DNA from a library consisting of monkey cell cDNA in the pcDNA 1 vector, 0.2 μg pSV2-neo DNA, and 10 μg mouse cell genomic (carrier) DNA, utilizing the calcium phosphate method (Graham et al., 1980). At 46 hrs after transfection, the medium was replaced with a selective medium [DMEM containing 10% fetal bovine serum and Geneticin (1 mg G418-sulfate/ml)]. The selective medium was changed every 3–4 days and neomycin-resistant ($Neo^R$) L-M colonies appeared 10–14 days after transfection.

Isolation of $DT^S$ L-M Cells $Neo^R$ L-M colonies were screened for DT sensitivity using a replica plating protocol (Naglich & Eidels, 1990). The $Neo^R$ L-M colonies were overlaid with a stack of three polyester-PeCap HD7-17 filter membranes and a layer of glass beads. The cells were allowed to grow through the filter membrane stack for seven days before they were screened for DT sensitivity. On the day of the screen, the stack of filters was carefully removed from the master dish, and the bottom filter was incubated with 2 μg DT/ml for 18 hours at 37° C. The DT-treated $Neo^R$ L-M colonies were washed with phosphate-buffered saline, calcium, magnesium (PBS/Ca/Mg; 8.8 mM $Na_2HPO_4$, 1.2 mM $KH_2PO_4$, 140 mM NaCl, 10 mM KCl, 0.5 mM $MgCl_2$, 1.0 mM $CaCl_2$, pH 7.4) and assayed for their ability to incorporate [$^{35}$S]-L-methionine into protein. The cells on the filters were precipitated using ice-cold 15% (w/v) trichloroacetic acid, treated with 1M sodium salicylate (pH 6.25) solution, dried in a 80° C. vacuum oven, and exposed to XAR-5 film for approximately 16 hours at −80° C. The colonies on the DT-treated filters were then stained with Coomassie G-250 and the stained colonies were compared to the corresponding areas on the fluorogram. Those colonies which appeared blue on the filter but had not been able to incorporate radiolabeled methionine (as indicated by a clear zone on the fluorogram) were isolated by cutting out the corresponding individual colonies from the middle membrane filter. The $DT^S$ mouse cells were amplified and re-screened three times using this replica plate protocol.

Southern Analysis

DNA isolated from the $DT^S$ mouse cells and from L-M cells was digested with an array of restriction enzymes utilizing the conditions described by the manufacturer. Digested DNA fragments were separated by agarose gel electrophoresis [0.7% (wt/vol)] (Sambrook et al., 1989) and were transferred to a Zeta-probe membrane (Southern, 1975). The probe, a 760 bp BglII cytomegalovirus immediate early promoter DNA fragment isolated from plink760 plasmid (Thomsen et al., 1984), was gel purified twice before being labeled with [$^{32}$P]-α-dCTP using an oligonucleotide labeling kit (specific activity of $1-2\times10^8$ cpm/μg). Hybridization was for 18 hours at 65° C. with 10 ng/ml radiolabeled DNA and 100 μg/ml sonicated salmon sperm DNA in 6× SSC (1× SSC=0.15M NaCl, 0,015M sodium citrate), 0.01M EDTA, 5× Denhardt's solution, and 0.5% SDS. After hybridization, filters were washed (Sambrook et al., 1989) and autoradiographed for 18 hours at −80° C. using XAR-5 film.

Cytotoxicity Assay

Cells were seeded in tissue culture dishes (48-well) and grown to confluency. Culture medium with 20 mM Hepes (Ph 7.4) containing varying amounts of DT, in the absence or presence of CRM 197 protein, was added to the cell monolayers and the cells were incubated at 37° C. for the indicated times. The monolayers were washed with PBS/Ca/Mg to remove unbound DT and incubated further in leucine-deficient MEM Eagle's medium for 1 hour. The cells were then incubated with [$^3$H]leucine for a final hour and subsequently washed, lysed, and assayed for [$^3$H]leucine incorporation into trichloroacetic acid-precipitable material (Proia et al., 1981; Eidels & Hart, 1982). All assays were done in triplicate.

DT Binding Assay

DT was radioiodinated by the Iodogen method (Cieplak et al., 1987); the specific activity of the radioiodinated DT was $1-2\times10^7$ cpm/μg. Cells were plated as described for the cytotoxicity assay. Plates containing confluent cell monolayers were placed on ice and washed twice with ice-cold PBS/Ca/Mg. The cells were then incubated with radioiodinated DT (25–200 ng/ml) in binding medium (Medium 199, 50 μg/ml bovine serum albumin (BSA), 100 μg/ml gelatin and 20 mM Hepes, Ph 7.4), in the absence or presence of increasing amounts of unlabeled competitor protein. The incubation was carried out for 5 hours at 4° C., and the cells were placed on ice and washed with ice-cold PBS/Ca/Mg to remove any unbound ligand. Cells were then solubilized in 0.2N NaOH, and the cell-associated radioactivity was measured (Middlebrook et al., 1978). Nonspecific association was defined by the radioactive DT that remained associated with the cells when the radiolabeled DT incubation was performed with 200-fold excess of unlabeled toxin. All assays were done in triplicate, and variation from the mean was 5–10%.

B. Results

Isolation of a $DT^S$ Mouse Cell Line After Transfection with Monkey Cell cDNA

A $DT^S$ mouse cell line was obtained after transfection of toxin-resistant L-M cells with a mixture of genomic DNA from highly toxin-sensitive monkey Vero cells and plasmid DNA containing a neomycin resistance gene (Naglich & Eidels, 1990). However, despite being subject to DT intoxication via the same pathway observed with naturally toxin-sensitive cells, these cells were only moderately sensitive to DT. They were further unable to bind radioiodinated toxin in a specific fashion. The absence of a full complement of Vero cell-derived DT receptors, due either to a lower level of expression of the transfected gene or to the presence of a truncated form of the gene, was hypothesized to underlie this lower sensitivity and lack of demonstrable specific binding.

To increase the probability of isolating $DT^S$ mouse cells with a full complement of DT receptors and to facilitate the subsequent cloning of the DT receptor gene, L-M cells were transfected with a cDNA library derived from Vero cells. Vero cells were chosen as a source of RNA for the construction of the cDNA library because they are extremely sensitive to DT and possess a large number of specific DT receptors.

L-M cells were transfected with a mixture of monkey cDNA and PSV2-neo DNA, as described in the Methods section. Stable $Neo^R$ transfectants were isolated and screened for DT sensitivity, utilizing a replica plate system. After screening approximately 8,000 colonies, one $DT^S$ mouse cell colony was isolated. The mouse cells from this colony, termed $DT^S$-I, were subcultured and purified three times using the replica plating assay (Table 1).

To confirm that these $DT^S$-I mouse cells contain Vero cell cDNA, Southern blotting analysis was performed. DNA from these cells was digested with an array of restriction enzymes, separated on an agarose gel, transferred to a nylon membrane, and probed with a [$^{32}P$]-labeled cytomegalovirus immediate early-promoter DNA sequence (Thomsen et al., 1984) under very stringent hybridization conditions (described in the Methods section). The DNA hybridization pattern obtained revealed that these cells contained vector sequences, a result consistent with the interpretation that the observed DT sensitivity phenotype was most likely due to the presence of a specific monkey cDNA in these cells.

Toxin Sensitivity

There is known to be a great variability in sensitivity to DT among different mammalian cell lines. For example, previously-isolated $DT^S$-I mouse cells (obtained after transfection with monkey cell genomic DNA) were found to be ~100fold less sensitive than Vero cells (Naglich & Eidels, 1990) The concentration of DT required to inhibit protein synthesis by 50% ($IC_{50}$) in those $DT^S$-I mouse cells was similar to that observed with cells of moderate toxin sensitivity (e.g., human and hamster cell lines).

TABLE 1

Characteristics of DT-sensitive mouse cells isolated from toxin-resistant populations.

| Cell Line | Source of DNA Used to Transfect L-M Cells | Number of $G418^R$ Colonies Screened[a] | Number of DT-Sensitive Colonies Isolated | Observed Frequency |
|---|---|---|---|---|
| $DT^s$-genomic[c] | Vero cells, genomic | 12,000 | 1 | $8.0 \times 10^{-5}$ |
| $DT^s$-I[d] | Vero cells, cDNA expression library | 8,000 | 1 | $1.3 \times 10^{-4}$ |
| | Hybrid [$DT^s$-I-COS] cells, plasmid DNA from pools: | | | |
| | I | 285 | 11 | $3.9 \times 10^{-2}$ |
| | II | 590 | 13 | $2.2 \times 10^{-2}$ |
| | III | 549 | 18 | $3.3 \times 10^{-2}$ |
| | IV | 231 | 0 | 0 |
| | V | 1,991 | 0 | 0 |
| $DT^s$-II | pDTS | 826 | 439 | 0.53 |

[a]$G418^R$ = G418 (a neomycin analog)-resistant.
[b]Observed frequency of $DT^s$ cells = number of $DT^s$ colonies isolated ÷ number of $G418^R$ colonies screened.
[c]Previously reported: Naglich and Eidels, 1990.
[d]Previously reported: Naglich et al., 1992.

Figure 1A:
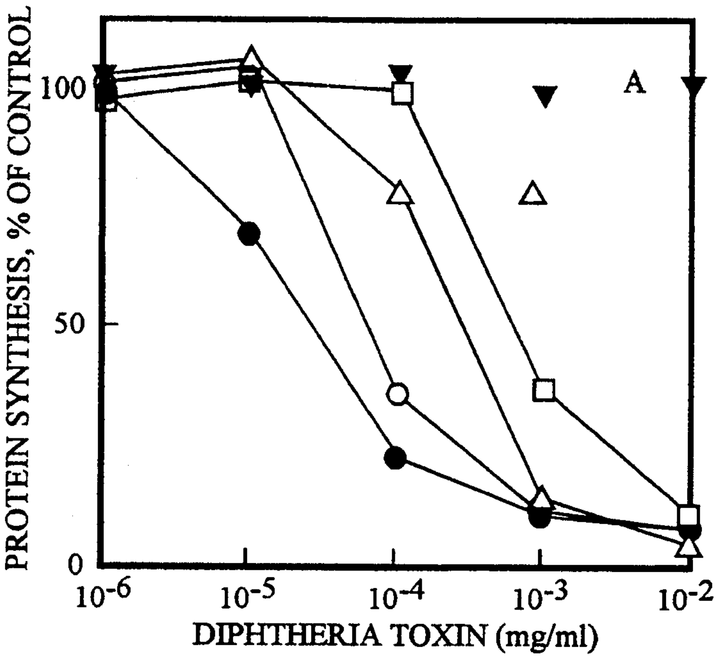
FIGS. 1A and 1B. DT-Mediated Toxicity and Protection by CRM 197 of $DT^S$ Mouse Cells and Vero Cells. Increasing amounts of DT were added to cells in the absence or presence of various concentrations of competitor CRM 197 protein. The cells were incubated for 1.5 hours at 37° C. and subsequently assayed for [$^3$H]leucine incorporation into trichloroacetic acid-(TCA-) precipitable material as described in the text. ( , , without CRM 197; (○), 1 μg/ml CRM 197; (Δ), 5 μg/ml CRM 197; and (□), 10 μg/ml CRM 197. Panel A: $DT^S$ mouse cells ( , ○, Δ, □); DT-resistant wild-type L-M cells ( ). Panel B: Vero cells. Results are expressed as the percentage of control protein synthesis in the absence of toxin ($DT^S$ mouse cells, 15,611 cpm; DT-resistant L-M cells, 33,654 cpm; and Vero cells, 11,552 cpm). The experiments shown in panels A and B were performed at the same time.
Figure 1B:
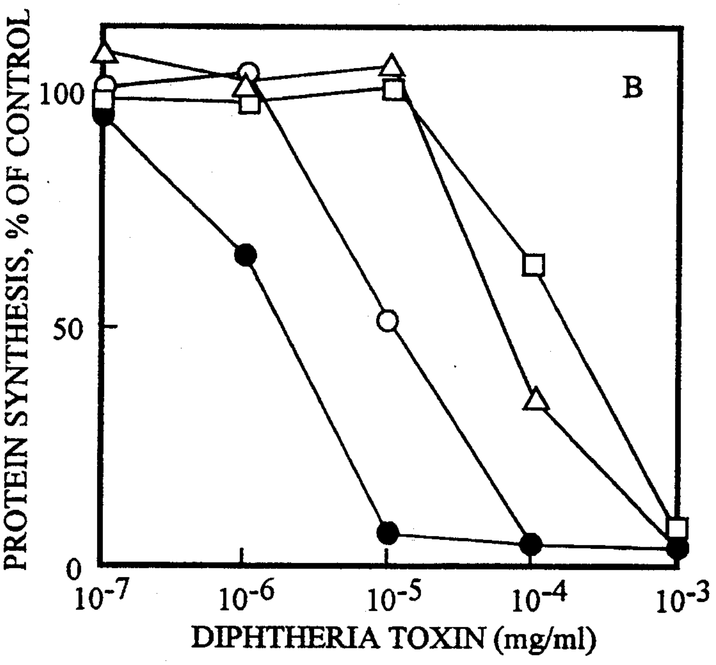

To determine the degree of toxin sensitivity of the $DT^S$-I mouse cell cDNA transfectants, an in vitro cytotoxicity assay was used. After incubation of the cells with DT at 37° C., it was observed that these cells were at least 1,000-fold more sensitive than wild-type L-M cells. An $IC_{50}$ of $3.1 \times 10^{-5}$ mg/ml was obtained with the $DT^S$-I cDNA transfectant mouse cells, in contrast to an $IC_{50}$ of $>10^{-2}$ mg/ml for the L-M cells (FIG. 1A). When the $IC_{50}$ of $DT^S$-I mouse cells was compared with that of Vero cells, the Vero cells were found to be ~10-fold more sensitive (FIG. 1B). These results indicated that the $DT^S$-I mouse cells obtained by transfection with monkey cDNA were considerably more sensitive to DT than wild-type L-M cells, and only slightly less sensitive to DT than Vero cells.

Protection of $DT^S$-I Mouse Cells by CRM 197

CRM 197 protein is a nontoxic analog of DT with an inactive A-fragment and a normal B-fragment (Ittelson & Gill, 1973; Mekada & Uchida, 1985), which binds to cell-surface toxin receptors and hence competes with active DT. If the $DT^S$-I mouse cells expressed specific DT receptors, CRM 197 should recognize them and compete with DT for binding. When these $DT^S$ mouse cells were incubated at 37° C. with DT in the presence of CRM 197, it was observed that these cells were protected in a dose-related fashion from the cytotoxic effects of DT (FIG. 1A). The dose-response curves each had the same shape and were shifted progressively to the right, as expected for a competitive inhibitor (Ittelson & Gill, 1973; Eidels & Hart, 1982; Schild, 1957; Draper et al., 1978). These observations strongly suggested that the $DT^S$-I mouse cells possessed specific cell-surface DT receptors.

Moreover, Schild analysis of the CRM 197 competition data (obtained from FIG. 1A) demonstrated that the DT receptors on the $DT^S$-I mouse cells bound DT with high affinity. The apparent dissociation constant was found to be $1.1 \times 10^{-8}$M, a value which is very similar to that reported for other naturally-occurring toxin-sensitive cells (Ittelson & Gill, 1973; Draper et al., 1978) and which differs only by a factor of 2 from the apparent dissociation constant of $5.3\times10^{-9}$ M calculated for Vero cells (data from FIG. 1B). The slope obtained from the Schild plot was 1.20 for the $DT^S$-I mouse cell data and 1.31 for the Vero cell data, values which are in good agreement with an expected slope of 1.0 for a competitive inhibitor (Schild, 1957).

Specific Binding of DT to the DT Receptor on $DT^S$-I Mouse Cells

The presence of specific functional DT receptors was further demonstrated by isolating the initial binding step in the in vitro cytotoxicity assay from the subsequent steps. Thus, DT ($10^{-6}$–$10^{-3}$ mg/ml) was first allowed to bind to the $DT^S$-I mouse cells at 4° C. (5 hours), a condition under which endocytic uptake is inhibited (Middlebrook et al., 1978). The cells were then washed to remove any unbound toxin and the temperature was shifted to 37° C. to allow any cell surface-bound DT to be internalized and translocated. Protein synthesis was inhibited ($IC_{50}=3.7\times10^{-5}$ mg/ml) in the $DT^S$-I mouse cells, whereas control wild-type L-M cells were unaffected. This demonstrated that DT did indeed originally bind, at 4° C., to functional cell-surface receptors.

Figure 2A:
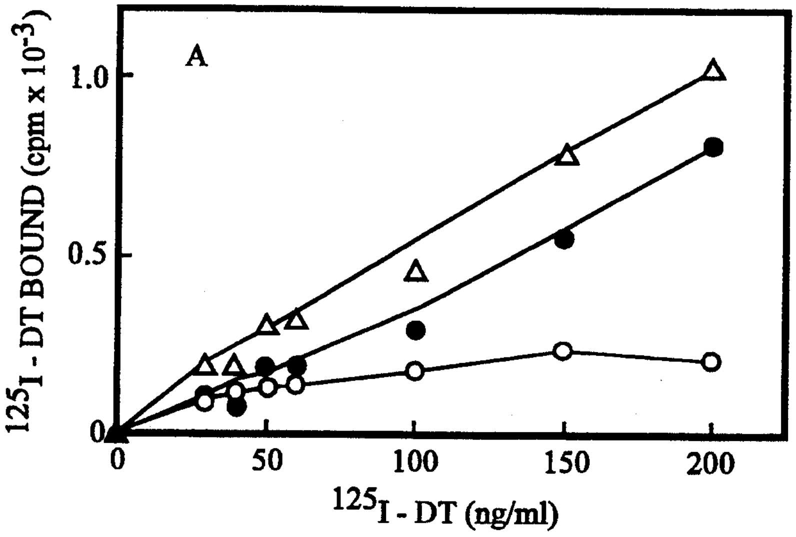
FIGS. 2A and 2B. Specific Binding of Radioiodinated DT to $DT^S$ Mouse Cells and Vero Cells. Cells were incubated at 4° C. with radioiodinated DT alone or with radioiodinated DT and a 200-fold excess of unlabeled DT in binding medium. After 5 hours the cells were washed with ice-cold PBS/Ca/Mg to remove unbound toxin and the radioactivity associated with the cells was assayed as described in the text. Panel A: $DT^S$ mouse cells; Panel B: Vero cells. Specific binding ( ) was determined by calculating the difference between the total binding with radioiodinated DT (Δ) and the nonspecific binding obtained with radioiodinated DT in the presence of excess unlabeled DT (○). The experiments shown in panels A and B were performed at the same time.
Figure 2B:
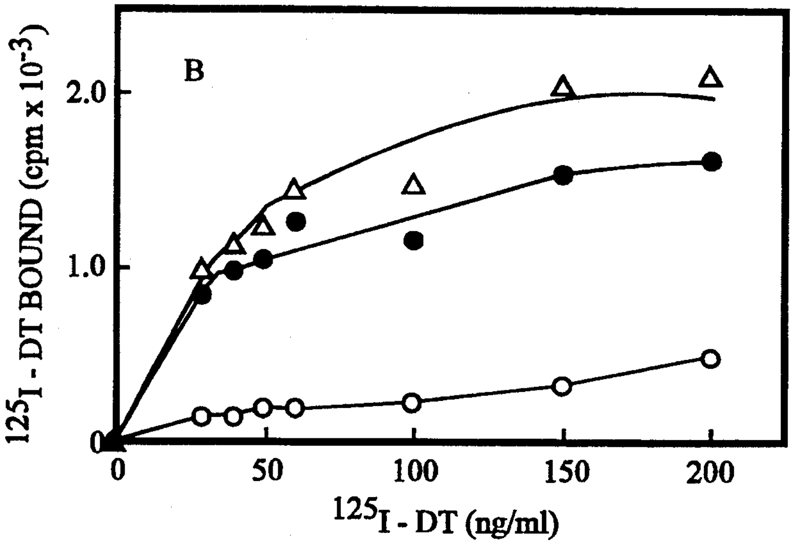

Middlebrook et al. (1978) have demonstrated that DT binding to Vero, BS-C-1, and MK-2 cells can be measured directly. With the exception of these cell lines (all of which are of monkey kidney origin), specific binding of radioiodinated DT to other cells has not been clearly demonstrated. To test directly for the presence of specific DT cell-surface receptors, the $DT^S$-I mouse cells were incubated at 4° C. (5 hours) with radioiodinated DT alone or with radioiodinated DT and a 200-fold excess of unlabeled DT. Specific binding of radioiodinated DT to cell-surface receptors on Vero cells and $DT^S$-I mouse cells could be readily detected (FIGS. 2A and B). The extent of binding and the percentage of specific binding obtained with the $DT^S$-I mouse cells (ranging from 40 to 70% of the total bound in a number of experiments) was readily demonstrable, whereas it is difficult to demonstrate such binding with all other toxin-sensitive cell lines except those of monkey origin. Although reproducible and readily measured, specific binding was not saturable at the concentrations employed and, therefore, the data were not amenable to accurate Scatchard analysis and the number of toxin binding sites on the $DT^S$-I mouse cells could not be determined.

Prevention of Radioiodinated DT Binding to $DT^S$-I Mouse Cells by HA6DT

Figure 3:
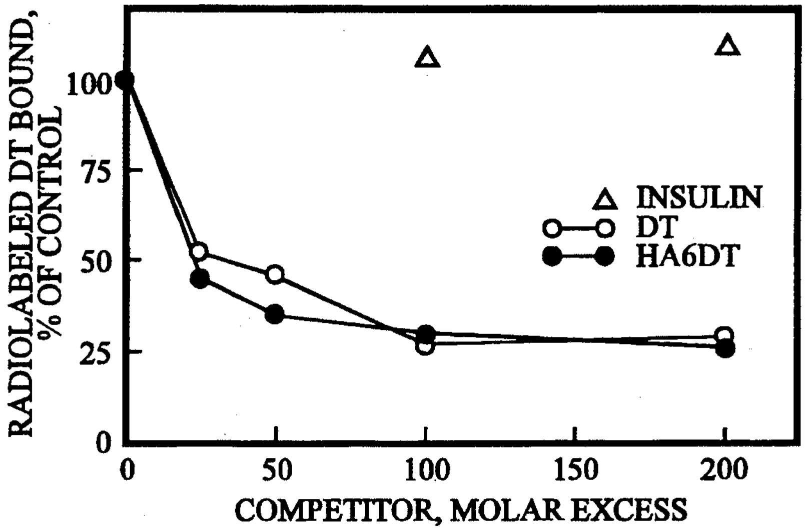
FIG. 3. Inhibition of Radioiodinated DT Binding to $DT^S$ Mouse Cells by HA6DT. $DT^S$ mouse cells were incubated for 5 hours at 4° C. in binding medium with 200 ng/ml ($3.4\times10^{-9}$M) of radioiodinated DT with increasing amounts of the unlabeled competitor protein as shown in the figure. The cells were washed to remove unbound ligands, and cell-associated radioactivity was assessed as described in the text. The average radioactivity bound in the absence of any competitor protein (100% control) was 1,247 cpm.

HA6DT, the $M_r$ 5,982 carboxyl-terminal receptor-binding domain of DT (obtained by hydroxylamine cleavage of DT), is known to protect Vero cells from the lethal action of DT by inhibiting DT binding to the Vero cell-surface toxin receptor (Rolf et al., 1990). To further characterize the DT receptor on the $DT^S$-I mouse cells, the ability of HA6DT to affect DT binding to $DT^S$-I cells was examined. HA6DT inhibited the binding of radioiodinated DT to the $DT^S$-I mouse cells as effectively as unlabeled DT; in contrast, insulin, an unrelated peptide with a molecular weight similar to that of HA6DT, had no effect on the binding (FIG. 3). This result demonstrated that the toxin-binding site of the receptor on the $DT^S$-I mouse cells was not only specific for DT but, more precisely, was specific for the receptor-binding region of DT.

The results presented herein are entirely consistent with the notion that the $DT^S$-I mouse cells—obtained after transfection with Vero cell-derived cDNA—bear toxin receptors with properties very similar to those widely acknowledged to be unique to the Vero cell DT receptor. These are: (i) functional DT receptors whose presence results in cells being highly sensitive to the toxin; (ii) DT receptors that are competed for by CRM 197 protein and by HA6DT peptide; and (iii) DT receptors that bind toxin in a highly specific fashion.

EXAMPLE II

Cloning, Sequencing and Analysis of the Vero Cell DT Receptor

Example I described the isolation of a DT-sensitive mouse cell line ($DT^S$-I) obtained by transfection of a wild-type DT-resistant population (L-M cells) with a cDNA expression library prepared from highly toxin-sensitive Vero cell RNA. Southern blot analyses of the DNA isolated from these cells confirmed that they contain several monkey cell cDNA inserts of different sizes. The present Example is directed firstly to the use of the $DT^S$-I cells and a plasmid-based rescue system to isolate the DT sensitivity gene, and secondly, to the sequencing and further characterization of the gene and its product.

A. Methods

Cell Fusion of $DT^S$ Mouse Cells with COS7 Cells and Isolation of Low-Molecular Weight DNA From the Hybrid (Fused) Cells Cell fusions were performed as previously described (Dawson et al., 1991) with modifications. Twenty-four hours prior to cell fusion (day 0), each well of a 6-well plate was seeded with a cell suspension consisting of a mixture of $DT^S$ mouse cells ($8\times10^5$ cells per well) and COS7 cells ($4\times10^5$ cells per well) in culture medium. The cells were incubated overnight (37° C.) and on the day of cell fusion (day 1), the cell monolayers were washed three times with PBS. PEG 1500 (0.5 ml per well) was added and spread evenly over the monolayers. After a 1 minute incubation at ambient temperature, the cell monolayers were washed exhaustively with wash medium (10% DMSO in culture medium) and were then incubated in fresh culture medium for 24 hours at 37° C. on day 2, the cells were detached from the wells by incubating with a solution of 0.05% (w/v) trypsin, 0.25% (w/v) EDTA for 5 minutes at ambient temperature. Individual cell pellets were pooled and resuspended in 4 ml culture medium. The cells (1 ml) were seeded in 100 mm diameter tissue culture dishes and incubated at 37 ° C.

On day 4, low-molecular weight DNA was recovered from the hybrid cells (Hirt, 1967; Margolskee et al., 1988), as follows. Cells were washed twice with 150 mM NaCl, 10 mM Tris-Hcl, Ph 7.5, lysed in lysis buffer (0.6% SDS, 10 mM EDTA, 10 mM Tris-Hcl, Ph 7.5) and incubated overnight at 4° C. Genomic DNA was removed by centrifugation at $14,000\times g$ for 50 minutes at 4° C. and the supernatant containing the low-molecular weight DNA was digested with proteinase K for 1 hour at 65° C. The digested material was then sequentially extracted twice with phenol, twice with phenol-chloroform-isoamyl alcohol (25:24:1) and twice with chloroform-isoamyl alcohol (24:1). Ammonium acetate was added to 2.5M and the DNA was precipitated with two volumes of ethanol for 18 h at −20° C. The DNA was the recovered by centrifugation at $14,000\times g$ for 1 hour, and the DNA pellets were washed three times with 70% ethanol, dried, and resuspended in 30 μl of double-distilled water.

Transformation of *E. coli*

Transformation of *E. coli* MC 1061/P3 cells was performed as recommended by Bio-Rad Laboratories utilizing their Gene Pulser apparatus. Low-molecular weight DNA (2 μl; obtained from the $DT^S$ mouse×COS7 hybrid cells) was added to ice-cold competent cells ($3\times10^{10}$ cells resuspended in 40 μl). The DNA:cell mixture was transferred to an ice-cold cuvette and a pulse was applied (settings=2.5 V; 200 ohm; 25 uFD). Immediately after pulsing, the cells were suspended in 1 ml Luria-Broth (LB) and shaken at 250 rpm at 37° C. for 1 hour. The transformed bacteria were then grown overnight on LB agar plates supplemented with ampicillin (50 μg/ml) and tetracycline (10 μg/ml). Transformations yielded approximately 150 ampicillin resistant ($Amp^R$)-tetracycline resistant ($Tet^R$) colonies per 2 μl of DNA.

Isolation of an *E. coli* Cell Containing the Individual cDNA Clone Encoding Toxin Sensitivity Recombinant *E. coli* colonies were grown overnight, transferred to Hybond N membranes and hybridized to the cytomegalovirus immediate-early promoter (CMV) DNA sequence (Thomsen et al., 1984) as described by Sambrook et al. (1989). Colonies that hybridized to the CMV DNA sequence were isolated and used to construct five independent pools (56 colonies/pool). Representative colonies from each pool were scraped into liquid medium and plasmid DNA was isolated and purified. Each DNA sample was used to transfect L-M cells and the transfected cells were then screened for DT sensitivity as described above. A pool that yielded $DT^S$ mouse cells was divided further, plasmid DNA isolated, and the DNA preparations from each subpool were then used to transfect L-M cells. The process was repeated until an individual *E. coli* colony was identified.

DNA Sequence Analysis

Gel-purified candidate cDNA fragments were subcloned in bacteriophage M13mp18 and M13mp19 vectors (Sambrook et al., 1989) and sequenced by the dideoxy chain termination method (Sanger et al., 1977) using the M13 universal sequencing primer or specific internal primers. Sequencing reactions were performed using either the Sequenase reagents (United States Biochemical) with [$^{35}S$]-labeled nucleotides or Taq polymerase with fluorescently-labeled nucleotides on an Applied Biosystems Model 373A DNA Sequencer. Oligonucleotides were constructed utilizing an Applied Biosystems Model 394 DNA/RNA Synthesizer.

Northern Blot Analysis

Total RNA was isolated from tissue culture cells by the guanidine thiocyanate/CsCl centrifugation procedure (Sambrook et al., 1989), and aliquots (25 μg of Vero or L-M; 18 μg of $DT^S$-II cell) were treated with 1M glyoxal/50% dimethylsulfoxide, electrophoresed through a 1.0% (w/v) agarose gel, and blotted onto a Zeta-Probe nylon membrane (Sambrook et al., 1989). Hybridization was performed at 42° C. for 20 hours using single-stranded [$^{32}P$]-labeled DNA probes (Sambrook et al., 1989) mixed with 100 μg/ml sonicated salmon sperm DNA in 50% (v/v) formamide, 5× SSPE (1× SSPE =150 mM NaCl, 10 mM sodium phosphate, 1 mM EDTA, pH 7.4), 5× Denhardt's solution, and 0.1% SDS. After hybridization, filters were washed in 2× SSC:0.5% SDS for 15 minutes at ambient temperature, in 2× SSC:1% SDS for 1 hour at 55° C., and in 2× SSC:0.1% SDS for 30 minutes at 65° C. (1× SSC=150 mM NaCl, 15 mM sodium citrate, pH 7.0); filters were exposed to Kodak XAR-5 film with or without an intensifying screen for 18 hours at −80° C.

Cross-linking of Radioiodinated Diphtheria Toxin Bound to Intact Cells

Toxin was chemically cross-linked to cell surface proteins as previously described (Cieplak et al., 1987). Briefly, tissue culture dishes (100 mm) containing confluent cell monolayers were placed on ice and washed three times with ice-cold PBS. The cells were then incubated with $^{125}I$-DT (250 ng/ml) in binding medium in the absence or presence of 100-fold excess unlabeled DT for 4 hours at 4° C. Unbound toxin was removed by three washes with ice-cold PBS. Toxin was then cross-linked to cell surface proteins using 0.2 mM DSS (prepared as a 20 mM stock in dimethyl sulfoxide); control cells lacking cross-linker received an equal amount of dimethyl sulfoxide. The monolayers were incubated for 35 minutes at 4° C. and then washed three times with ice-cold Tris-buffered saline (10 mM Tris-HCl, 150 mM NaCl, pH 7.5) followed by three washes using ice-cold PBS. Cells were then scraped off the dishes in ice-cold PBS and pelleted by centrifugation. Cell pellets were lysed by treatment with 0.25 ml electrophoresis sample buffer [2% (w/v) SDS, 10% (v/v) glycerol, 62.5 mM Tris-HCl (pH 6.8)] and heated for 3 min at 100° C. Radiolabeled cross-linked proteins were resolved by SDS-PAGE on 8% polyacrylamide gels and visualized by autoradiography. Autoradiography was performed at −80° C. using Kodak X-Omat film and Du Pont Cronex Lightning Plus intensifying screens.

B. Results

Isolation of DT Sensitivity-Conferring Plasmid

After screening the L-M cell transfectants for DT sensitivity, employing the replica plate protocol described above, it was observed that three out of the five plasmid DNA pools used to transfect L-M cells yielded DT-sensitive colonies (Table 1). For example, pool III gave 18 DT-sensitive colonies out of 549 neomycin-resistant colonies, representing a frequency of $3.3\times10^{-2}$, a greater than 300-fold enrichment for a plasmid conferring DT sensitivity as compared to the original cDNA library. Screening ~30,000 L-M cell colonies transfected with the vector alone did not reveal any spontaneous DT-sensitive colonies.

To isolate a single cDNA responsible for DT sensitivity, bacterial colonies from one of the positive pools were divided into subpools and plasmid DNA was isolated. L-M cells were transfected with these plasmid DNA preparations, and the transfected L-M cells were again screened for DT sensitivity. Positive pools were identified, further subdivided, and tested until a single plasmid (pDTS) capable of conferring DT sensitivity was isolated. When pDTS was transfected into L-M cells, it conferred DT sensitivity with a high frequency (0.53; Table 1). From this experiment, one $DT^S$ mouse cell colony was purified by the replica plate protocol; this purified cell line ($DT^S$-II) was employed in subsequent experiments (Table 1).

Toxin Sensitivity of $DT^S$-II Cells Transfected With pDTS Plasmid DNA

To assess the degree of DT sensitivity of the $DT^S$-II cells, an in vitro cytotoxicity assay was employed. The $IC_{50}$ obtained with $DT^S$-II cells was at least 2,000-fold lower than that obtained with L-M cells; an $IC_{50}$ of 4.7 ng/ml was obtained with the $DT^S$-II mouse cells compared to an $IC_{50}$ of $>10^4$ ng/ml for L-M cells (Table 2). When the $IC_{50}$ of the $DT^S$-II cells and Vero cells was compared, the $DT^S$-II cells were found to be virtually as DT sensitive as Vero cells (Table 2).

Protection of Toxin-sensitive Cells from DT-Mediated Cytotoxicity by CRM 197

The initial step of DT intoxication is the binding of the toxin, via its B-fragment, to a specific cell-surface receptor. CRM 197, a nontoxic analog of DT, has an inactive A-fragment and a normal B-fragment that competes with DT for binding to receptors (Mekada & Uchida, 1985; Naglich & Eidels, 1990; Rolf et al., 1990). When $DT^S$-II cells were incubated with varying amounts of DT in the presence of CRM 197 (5 μg/ml) and assayed for protein synthesis, CRM 197 afforded considerable protection; an $IC_{50}$ of 39 ng/ml was obtained with $DT^S$-II cells when incubated with DT in the presence of CRM 197 compared to an $IC_{50}$ of 4.7 ng/ml when incubated with DT alone (Table 2). A similar effect was observed with Vero cells; an $IC_{50}$ of 100 ng/ml was obtained with Vero cells incubated with DT in the presence of CRM 197 compared to an $IC_{50}$ of 4 ng/ml when incubated with DT alone.

Trypsin-Treatment of DT-Sensitive Cells

The DT receptor is known to have a protein component which is trypsin- and pronase-sensitive (Moehring and Crispell, 1974; Cieplak et al., 1987). Trypsin-treated $DT^S$-II cells were found to be less sensitive to DT than untreated cells; an $IC_{50}$ of 29 ng/ml was obtained with trypsin-treated $DT^S$-II cells compared to an $IC_{50}$ of 4.7 ng/ml for untreated cells (Table 2). A similar effect was observed with Vero cells; an $IC_{50}$ of 19 ng/ml was obtained with trypsin-treated Vero cells compared to an $IC_{50}$ of 4 ng/ml for untreated cells (Table 2).

TABLE 2

Toxin sensitivity of $DT^s$-II cells, Vero cells and L-M cells, and the protective effects of the competitor protein CRM 197 and of trypsin-treatment.

| Cell Line | CRM 197[a] | Trypsin Treatment | DT $IC_{50}$[c] (ng/ml) |
|---|---|---|---|
| $DT^s$-II | − | − | 4.7 |
| | + | − | 39 |
| | − | + | 29 |
| Vero | − | − | 4 |
| | + | − | 100 |
| | − | + | 19 |
| L-M | − | − | >10,000 |

[a]Increasing amounts of toxin were added to the cells in the absence or present of 5 μg/ml competitor CRM 197 protein. The cells were incubated for 1.5 h at 37° C. and were subsequently assayed for their ability to incorporate [$^3$H]-leucine into TCA-precipitable material as described in Experimental Procedures.

[b]Confluent cell monolayers were washed with PBS and were treated with trypsin (2.5 μg/ml in PBS) for 30 min at 37° C. Culture medium was then added to the cell monolayers and the plates were centrifuges (5 min at ambient temperature, 460 × g) to prevent detachment of the cells from the wells. The cell monolayers were washed twice with PBS before varying amounts of DT were added. The cells were incubated for 1.5 h at 37° C. and were subsequently assayed for their ability to incorporate [$^3$H]-leucine into TCA-precipitable material as described in Experimental Procedures.

[c]Concentration of DT required to inhibit protein synthesis by 50%.

Acid-Shock Receptor-Dependent Penetration of DT

Figure 4:
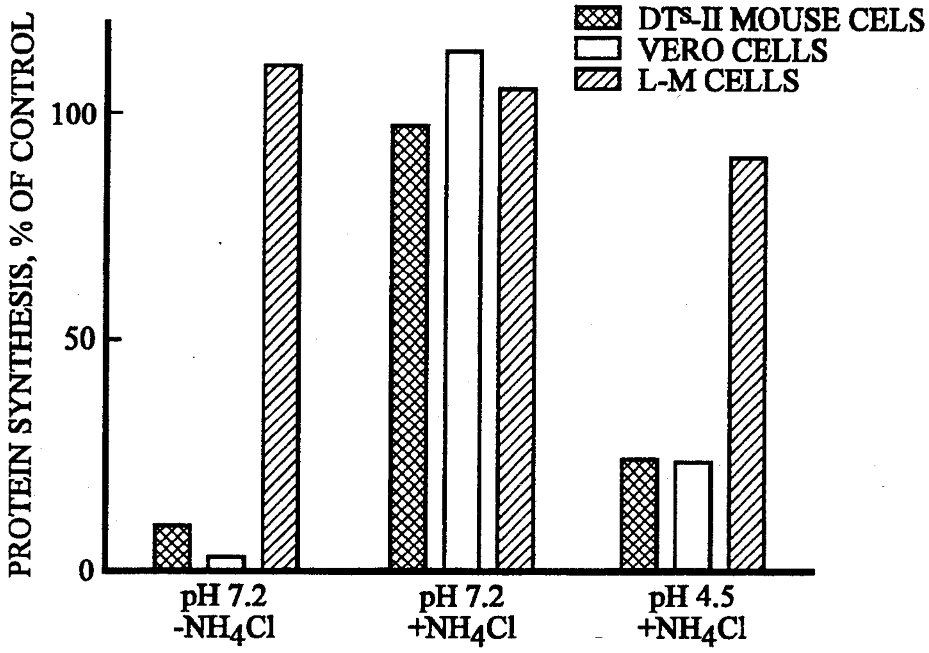
FIG. 4. Effect of Ammonium Chloride and Effect of Exposure to an Acidic Medium on the Cytotoxic Activity of Receptor-Bound Toxin. Cells were bound with nicked toxin (100 ng/ml) at 4° C. for 4 hours and then washed with PBS to remove unbound toxin. The treated cells were then incubated at 37° C. for 10 minutes at pH 7.2 in the presence (+) or absence (−) of 10 mM ammonium chloride, or at pH 4.5 in the presence (+) of 10 mM ammonium chloride. Cells were then washed and incubated at 37° C. for 2 hours in leucine-deficient medium with (+) or without (−) ammonium chloride. The cells were subsequently assayed for [$^3$H]-leucine incorporation into TCA-precipitable material. The results are expressed as the percentage of control protein synthesis in the absence of toxin for each cell line.

DT bound to specific receptors on toxin-sensitive cells is normally endocytosed into intracellular vesicles whose acidification results in a toxin conformational change that leads to translocation of the A-fragment into the cytosol (Draper & Simon, 1980; Sandvig & Olsnes, 1980; Stemark et al., 1988). Lysosomotropic amines such as chloroquine and ammonium chloride protect toxin-sensitive cells from DT cytotoxicity by raising the pH within acidic vesicles. It was of interest to determine whether ammonium chloride protected $DT^S$-II cells against intoxication. In the presence of 10 mM ammonium chloride, the $DT^S$-II cells are protected against DT cytotoxicity (FIG. 4, closed bars; pH 7.2, $+NH_4Cl$). This result is similar to that observed with Vero cells (FIG. 4, open bars; pH 7.2, $+NH_4Cl$) and suggests that DT bound to the cell surface of these cells is endocytosed into acidified vesicles before being translocated into the cytosol.

Since the low-pH environment of the endocytic vesicles can be mimicked by acidifying the culture medium surrounding the cells to pH 4.5 (Draper & Simon, 1980; Sandvig & Olsnes, 1980), the inventors examined whether the protective effect of ammonium chloride observed with $DT^S$-II cells could be bypassed by acidifying the culture medium and allowing toxin to translocate through the plasma membrane. After the medium pH was briefly shifted from 7.2 to 4.5, in the presence of ammonium chloride, receptor-bound DT was able to enter $DT^S$-II cells directly and inhibit protein synthesis (FIG. 4, closed bars; pH 4.5 $+NH_4Cl$). Under these same acid-shock conditions, protein synthesis in Vero cells was reduced by receptor-bound DT (FIG. 4, open bars; pH 4.5 $+NH_4Cl$), and untransfected L-M cells remained resistant to DT intoxication (FIG. 4, hatched bars; pH 4.5 $+NH_4Cl$).

Figures 5A, 5B:
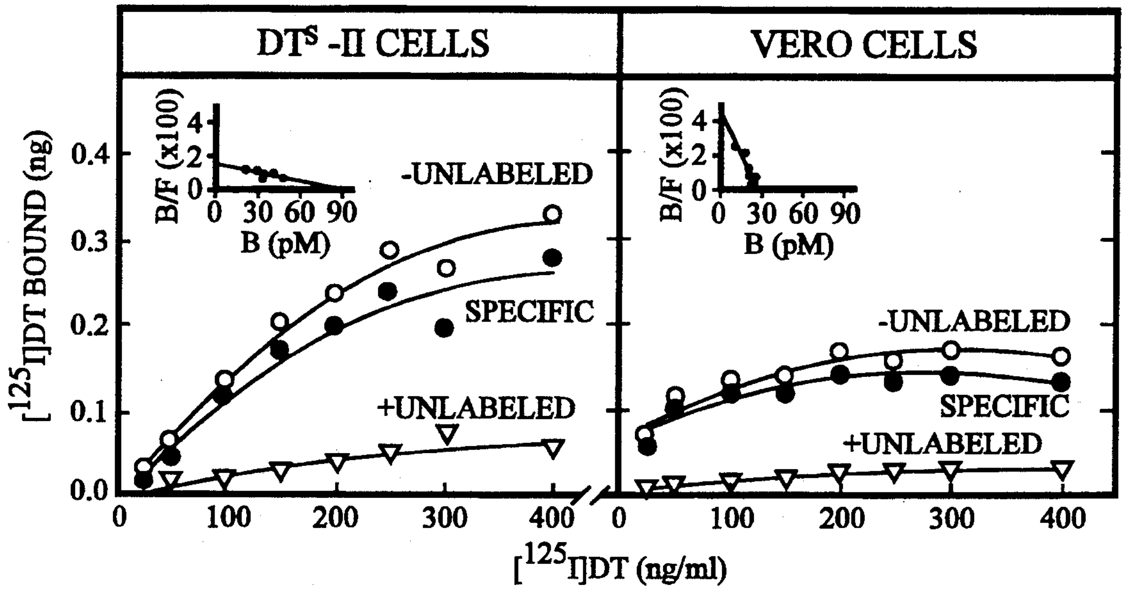
FIGS. 5A and 5B. Specific Binding of Radioiodinated DT to $DT^S$-II Cells and Vero Cells. Cells were incubated at 4° C. with $^{125}$I-DT alone or with $^{125}$I-DT in the presence of 100-fold excess of unlabeled DT in binding medium. After 5 hours, the cells were washed with ice-cold PBS to remove unbound toxin, and the radioactivity associated with the cells was assayed. Panel A: $DT^S$-II cells; Panel B: Vero cells. Specific binding ( ) was determined by calculating the difference between the total binding with $^{125}$I-DT (○) and the nonspecific binding obtained with $^{125}$I-DT in the presence of excess unlabeled DT (▽). Insets: Scatchard analysis of the data presented in the panel. The concentrations of specifically bound $^{125}$I-DT (B) are plotted on the abscissa and bound/free toxin (B/F) on the ordinate. Data was fitted by regression analysis. The experiments shown in both panels were performed in triplicate and at the same time. The specific activity of the $^{125}$I-DT employed was $1.66\times10^4$ cpm/ng.

Specific Binding of Radioiodinated DT to the Cell-Surface Receptors on $DT^S$-II Cells The $DT^S$-II cells bear functional receptors that bind DT and mediate toxin action (FIG. 4). To test directly for the presence of specific cell-surface DT receptors, $DT^S$-II cells and Vero cells were incubated with $^{125}$I-DT or with $^{125}$I-DT in the presence of 100-fold excess of unlabeled DT. Specific binding of $^{125}$I-DT to receptors could be readily detected on $DT^S$-II cells (FIG. 5A, closed circles) as well as on Vero cells (FIG. 5B, closed circles). The specific binding of $^{125}$I-DT to $DT^S$-II cell and to Vero cell receptors was saturable, and the extent of specific binding of $^{125}$I-DT obtained with $DT^S$-II cells was approximately two-fold greater than that obtained with Vero cells. Scatchard analyses revealed that both of these cells possess a single class of high-affinity receptors; ~54,000 receptors per $DT^S$-II cell with an apparent $K_d$ of $5.8\times10^{-9}$M (FIG. 5A, inset), whereas Vero cells possess ~17,000 receptors per cell with an apparent $K_d$ of $5.9\times10^{-10}$M (FIG. 5B, inset).

Despite the fact that $DT^S$-II cells bear 54,000 DT receptors whilst Vero cells display only 17,000 receptors, the $DT^S$-II cells are not more sensitive than Vero cells (Table 2). This lack of greater sensitivity may be due to the lower affinity of the receptors on the $DT^S$-II cells compared to the receptors on Vero cells, possibly due to a different subunit structure of the DT receptor among these cells. Alternatively, this lack of greater sensitivity may be due to another step in the intoxication process that is rate limiting. In this context, it has been recently shown that Vero cells display $7.5\times10^6$ copies per cell of a DT receptor-associated protein ($M_r$ 27,000) involved in the cytotoxic process subsequent to DT binding, while L-M cells display only 1,900 molecules of this ancillary protein per cell (Iwamoto et al., 1991). Although the $DT^S$-II cells (which are derived from L-M cells) have a large number of DT binding sites, they may bear too small a number of this post-binding cell-surface component; the insufficient amount of this component may be the rate-limiting step in the cytotoxicity process. Such a second post-binding component had been previously identified employing an anti-idiotypic antibody which protected Vero cells by preventing internalization of cell-surface bound DT (Rolf et al., 1989).

Chemical Cross-Linking of Radioiodinated DT to Surface Proteins

To provide information about the nature of DT receptors expressed on $DT^S$-II cells, both $^{125}$I-DT and a homobifunctional, non-cleavable cross-linking reagent, disuccinimidyl suberate (DSS) were employed. DSS has been successfully used in the characterization of several cell surface receptors (Fukunaga et al., 1990;Matthews and Vale, 1991; Squinto et al., 1991), including the DT receptor on Vero cells (Cieplak et al., 1987).

Figure 6A:
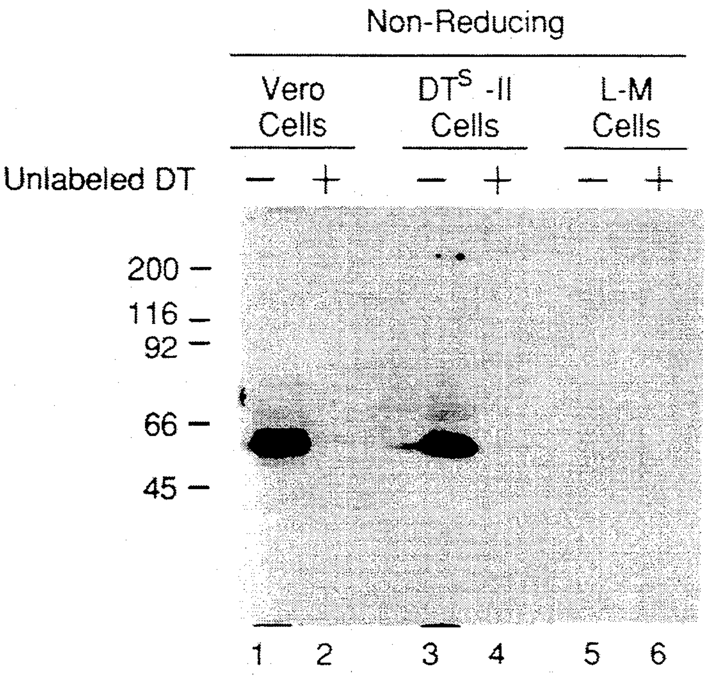
FIGS. 6A to 6C. Covalent Cross-Linking of Radioiodinated Toxin to Surface Proteins of Vero, $DT^S$-II, and L-M Cells. Cells were incubated at 4° C. with unnicked $^{125}$I-DT (250 ng/ml) alone (−) or with $^{125}$I-DT in the presence of 100-fold excess of unlabeled DT (+) in binding medium. After 4 hours, the cells were washed with ice-cold PBS to remove unbound toxin and chemical cross-linking was performed with the bifunctional cross-linking reagent DSS. The cross-linked species were then separated by electrophoresis on polyacrylamide gels in the presence of SDS and visualized by autoradiography. In Panel A the samples were analyzed without prior reduction, and in Panels B and C the samples were reduced with 5% 2-mercaptoethanol prior to electrophoresis. Each lane contained lysates obtained from an equivalent number of cells. The experiments shown in Panels A and B were performed with the same cell lysates and at the same time. In panels A and B, Vero cells (lanes 1 and 2); $DT^S$-II cells (lanes 3 and 4); L-M cells (lanes 5 and 6). Panel C represents an independent experiment in which Vero cells were incubated with $^{125}$I-DT in the absence (lane 1) or presence (lane 2) of cross-linking agent. The position of the $M_r$ ~80,000 cross-linked product(s) is denoted with an asterisk. The mobility of the molecular weight markers are given on the left margin in kilodaltons: myosin (200); β-galactosidase (116); phosphorylase b (92); bovine serum albumin (66); and ovalalbumin (45).

When $^{125}$I-DT was bound to $DT^S$-II, Vero, and L-M cells and covalently cross-linked with DSS, higher molecular weight bands were detectable, in addition to the major DT band ($M_r$ 60,000), in $DT^S$-II cell extracts and in Vero cell extracts (FIG. 6A & B, lanes 1 and 3). In contrast, the higher molecular weight cross-linked proteins and the major radiolabeled DT band were not detectable in untransfected L-M cell extracts (FIG. 6A & B, lane 5). When the Vero cell extracts were analyzed under nonreducing conditions, the apparent $M_r$ of DT was 56,000, while the apparent $M_r$ of the predominant cross-linked high-molecular weight bands were 70,000 and 84,000, respectively (FIG. 6A, lane 1), corresponding (by difference) to two toxin-binding proteins with $M_r$ of ~14,000 and ~28,000. The appearance of these bands could be specifically and almost completely inhibited when the cells were incubated with 100-fold excess unlabeled DT during the binding of $^{125}$I-DT (FIG. 6A, lane 2). When the $DT^S$-II cell extracts were analyzed under nonreducing conditions, one distinct band with a $M_r$ of ~70,000 was observed (FIG. 6A, lane 3), corresponding to a DT-binding protein with a $M_r$ of ~14,000. The appearance of this band could be specifically inhibited when the cells were incubated with 100-fold excess unlabeled DT (FIG. 6A, lane 4).

Figure 6B:
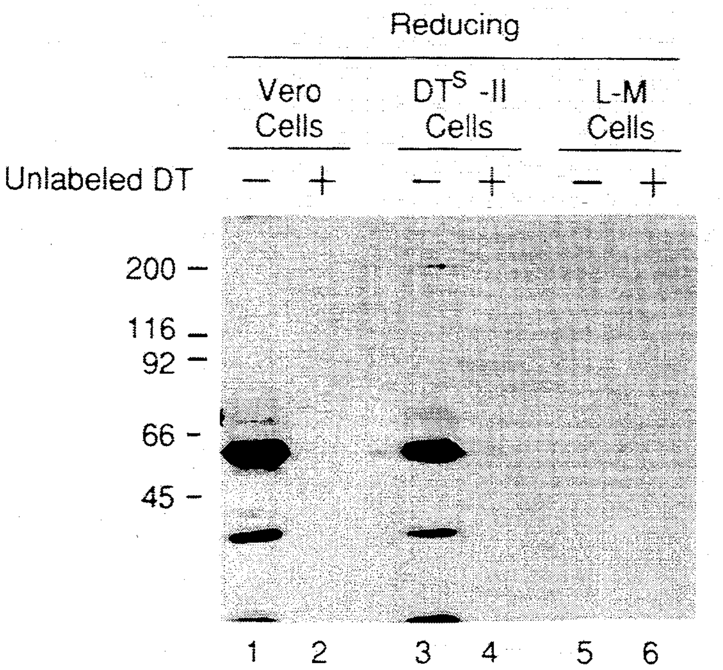
Figure 6C:
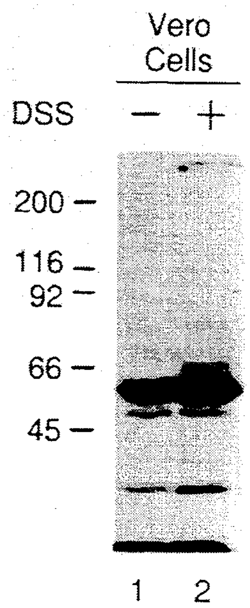

When the same cross-linked extracts from Vero cells were analyzed under reducing conditions, both the high-molecular weight proteins and the major DT band ($M_r$ 58,000) were again detectable (FIG. 6B, lane 1). The cross-linked protein with a $M_r$ of 70,000 was readily visible; however, the $M_r$ ~84,000 band present in the non-reduced gel exhibited a slightly increased electrophoretic mobility and appeared as a diffuse band with an average $M_r$ of ~82,000 (FIG. 6B, lane 1). These results are consistent with the presence of DT-binding proteins with $M_r$ of ~12,000 and ~24,000 on Vero cells. When the $DT^S$-II extracts were analyzed under reducing conditions, the band with a $M_r$ of 70,000 was readily detected (FIG. 6B, lane 3), indicative of a DT-binding protein with a $M_r$ of ~12,000. The higher $M_r$ bands were absent when both Vero cells (FIG. 6C, lane 1) and $DT^S$-II cells were allowed to bind the radiolabeled toxin but not treated with the cross-linking reagent.

The difference in the cross-linking pattern of DT to cell surface proteins may represent either related proteins that differ in post-translational modification(s), or, the common lower molecular weight protein may be the result of differential processing of the larger DT-binding protein. The difference in cross-linking pattern observed herein may represent tissue-specific differential processing, such as has been reported for the EGF/TGF-α family of growth factor precursors (Massague, 1990; Mroczkowski et al., 1989).

Alternatively, the two cross-linked proteins on Vero cells may represent two distinct subunits of a receptor complex, only one of which has been transfected into the $DT^S$-II cells. Mekada et al. (1991) and Iwamoto et al. (1991) have recently described proteins of $M_r$ 14,500 and 27,000, respectively, on Vero cells that participate in the DT intoxication process. These proteins may represent the cross-linked proteins detected herein.

Nucleotide and Predicted Amino Acid Sequence of the Monkey Cell cDNA Encoding DT Sensitivity Plasmid pDTS contains a 1,063 base pair monkey cell cDNA insert (FIG. 7; SEQ ID NO:1). Nucleotide sequence analysis revealed a 5' untranslated region of 58 nucleotides, a 3' untranslated region of approximately 381 nucleotides, and an open reading frame of 624 nucleotides (nucleotide position 59–682) coding for a protein of 208 amino acids (FIG. 7; SEQ ID NO. 1 & 2).

The methionine codon (ATG) at nucleotide position 59 is in a favorable context for translation initiation (Kozak, 1987). This methionine is followed by a characteristic signal sequence (yon Heijne, 1986) of 23 amino acid residues. A presumed extracellular domain consists of 136 residues (amino acid position 24–159), followed by a putative transmembrane domain of 25 residues (amino acid position 160–184) that is flanked by basic residues (Sabatini et al., 1982), and followed by a carboxyl-terminal cytoplasmic domain of 24 residues (amino acid position 185–208). Placement of the amino-terminus outside the cell is based on the presence of a classic signal sequence at this end and on the observation that cysteine-rich EGF-like repeat sequences typically function in the extracellular milieu, either in external domains of cell-surface proteins or in secreted proteins (Hobbs et al., 1990).

The mature protein, after cleavage of the signal peptide, would yield an integral membrane protein of 185 amino acids with a calculated $M_r$ of 20,652 and a quite basic isoelectric point of 9.9. Salient features identified in the extracellular domain include: (i) a series of serine and threonine residues which are potential sites for O-glycosylation (Kornfeld & Kornfeld, 1980); (ii) a cluster of positively charged amino acid residues, between $Pro_{86}$ and $Pro_{107}$, which could serve as potential sites of proteolysis by trypsin-like enzymes; and (iii) a cysteine-rich region of six cysteine residues ($Cys_{108}$, $Cys_{116}$, $Cys_{121}$, $Cys_{132}$, $Cys_{134}$, and $Cys_{143}$), the spacing of which—$CX_7CX_4CX_{10}CX_1CX_8C$—is the hallmark motif of a number of growth factors belonging to the EGF/TGF-α family (Doolittle, 1985; Shoyab et al., 1989).

Interestingly, there is a single/unpaired cysteine residue ($Cys_{174}$) in the transmembrane domain (FIG. 7). Unpaired cysteines are not uncommon in transmembrane domains of cell surface proteins (Davis & Linzer, 1989; Kaufman et al., 1984; Klein et al., 1989; Nef et al., 1988) and are also present in the transmembrane domain of the human EGF precursor (Bell et al., 1986) and the human TGF-α precursor (Derynck et al., 1984). Cysteine residues in the transmembrane region of some major histocompatibility antigens are fatty acylated via a thioester bond (Kaufman et al., 1984). In most other cases, however, it is not clear whether the unpaired cysteine residues are found free or are involved in disulfide bonding to form homo- or heterodimers (Weissman et al., 1988a, 1988b).

In the case of the DT receptor, comparing the results obtained by cross-linking in the absence and presence of reducing agents, suggests that the cysteine in the DT receptor is probably not involved in dimer formation. One possible function for the free cysteine in the receptor's transmembrane domain could be the reduction of the interchain disulfide bond linking the A and B fragments of DT. Evidence has been provided for the participation of membrane sulfhydryl groups in the interchain reduction (Wright et al., 1984; Ryser et al., 1991), and a close correlation has been described between interchain disulfide reduction and toxin translocation (Moskaug et al., 1987). Thus, the free cysteine in the transmembrane domain of the DT receptor would be properly positioned to catalyze the reductive cleavage of the A-B disulfide bond after the low pH-induced insertion of the B fragment into the endosomal membrane and concomitant with the translocation of the A fragment across this membrane.

Multiple lines of evidence suggest that tyrosine residues in the cytoplasmic domain of receptors that mediate endocytosis are essential for internalization (Davis et al., 1987; Lobel et al., 1989; Jing et al., 1990; Breitfeld et al., 1990; Chen et al., 1990). It has been demonstrated that the tyrosine-containing signals required for rapid endocytosis form well-ordered β-turns essential for internalization. These include the NPXY sequence of the LDL receptor (Bansal & Gierasch, 1991) and the PPGY sequence of lysosomal acid phosphatase (Eberle et al., 1991); in the latter case, the tyrosine residue is located 8 amino acids away from the transmembrane domain. The cytoplasmic domain of the DT receptor has two tyrosine residues (FIG. 7), one of which ($Tyr_{192}$) is located 8 amino acids away from the transmembrane domain and is part of the sequence GGY, suggesting that this GGY sequence could be involved in the β-turn formation necessary for receptor-mediated endocytosis.

Comparison of the Predicted Amino Acid Sequence Derived from the DT Sensitivity Gene with that of Growth Factors Computer-based comparison of the relatedness of the predicted amino acid sequence of the above-described monkey DT sensitivity protein (DTS-P) revealed that it corresponds to a precursor of human HB-EGF (Higashiyama et al., 1991). Detailed comparison of the amino acid sequence of the DTS-P and the HB-EGF precursor revealed an overall sequence identity of 97%, corresponding to only six differences (FIG. 7). Mature HB-EGF is a member of the EGF-family of growth factors which competes with EGF for binding to the EGF receptor (Higashiyama et al., 1992). Secreted HB-EGF is mitogenic for BALB-3T3 fibroblasts and smooth muscle cells but not endothelial cells (Higashiyama et al., 1991).

It has been suggested and in some cases shown that growth factor precursors, as integral plasma membrane proteins, can function in the regulation of cell growth and differentiation as well as in cell-cell interactions (Brachmann et al., 1989; Massague, 1990;Mroczowski et al., 1989; Plowman et al., 1990; Wong et al., 1989). For example, the TGF-α precursor is present on the cell surface where it is processed into the mature growth factor; however, the proteolytic process that releases mature TGF-α is inefficient in many cell types and thus substantial levels of the TGF-α precursor can accumulate on the cell surface (Brachmann et al., 1989; Pandiella & Massague, 1991; Wong et al., 1989).

The cell surface form of the TGF-α precursor has been reported to be a biologically active ligand which can bind to EGF/TGF-α receptors located on the surface of adjacent cells (Brachmann et al., 1989; Wong et al., 1989). However, it has not been demonstrated whether the cell surface TGF-α precursor can itself function as a receptor for some other ligand (Pandiella & Massague, 1991). Furthermore, prior to the present study, the re-internalization of any cell surface growth factor precursor had not been demonstrated.

Expression of the DT Sensitivity mRNA

To assess expression of the mRNA corresponding to the monkey cell cDNA insert of plasmid pDTS, blot hybridization analysis of total RNA obtained from Vero, $DT^S$-II and L-M cells was performed. Using the 1,063 base pairs monkey cell cDNA as a probe, two mRNA species corresponding to 2.0 and 2.6 kb were detected in Vero cells (FIG. 8, lane 1), whereas no specific transcripts were detected in L-M cells (FIG. 8, lane 3). Several abundant transcripts ranging in size from ~1.0 to ~4.0 kb were detected in $DT^S$-II cells (FIG. 8, lane 2). Discrete transcripts in $DT^S$-II cells could not be detected even after shorter exposure times; the molecular basis for this heterogeneity is not clear. These results show that the DT sensitivity gene is expressed in the $DT^S$-II cells and in Vero cells but is not expressed at detectable levels in L-M cells.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Bansal, A., and Gierasch, L. M. (1991) Cell 67, 1195–1201.

Bell, G. I., Fong, N. M., Stempien, M. M., Wormsted, M. A., Caput, D., Ku, L., Urdea, M. S., Rall, L. B., and Sanchez-Pescador, R. (1986) Nucl. Acids Res. 14, 8427–8446.

Brachmann, R., Lindquist, P. B., Nagashima M., Kohr, W., Lipari, T., Napier, M., and Derynck, R. (1989) Cell 56, 691–700.

Breitfield, P. P., Casanova, J. E., McKinnon, W. C., and Mostov, K. E. (1990) J. Biol. Chem. 265, 13750–13757.

Chen, W. J., Goldstein, J. L., and Brown, M. S. (1990) J. Biol. Chem. 265, 3116–3123.

Cieplak, W., Gaudin, H. M., and Eidels, L. (1987) J. Biol. Chem. 262, 13246–13253.

Collier, R. J. (1975) Bacteriol. Rev. 39, 54–85.

Davis, C. G., van Driel, I. R., Russell, D. W., Brown, M. S., and Goldstein, J. L. (1987) J. Biol. Chem. 262, 4075–4082.

Davis, J. A., and Linzer, D. I. H. (1989) Mol. Endocrinol. 3, 674–680.

Derynck, R., Roberts, A. B., Winkler, M. E., Chen, E. Y., and Goeddel, D. V. (1984) Cell 38, 287–297.

Dawson P. A., Metherall, J. E., Ridgway, N. D., Brown, M. S., and Goldstein, J. L. (1991) J. Biol. Chem. 266, 9128–9134.
Doolittle, R. F. (1985) Trends in Biochem. Sci. 10, 233–237.
Draper, R. K., Chin, D., Stubbs, L., and Simon, M. J. (1978) J. Supramol. Struct. 9, 47–55.
Eberle, W., Sander, C., Klaus, W., Schmidt, B., von Figura, K., and Peters, C. (1991) Cell 67, 1203–1209.
Eidels, L. , Proia, R. L., and Hart, D. A. (1983) Microbiol. Rev. 47, 596–620.
Eidels, L., and Hart, D. A. (1982) Infect. Immun. 37, 1054–1058.
Fukunaga, R., Ishizaka-Ikeda, E., Seto, Y., and Nagata, S. (1990) Cell 61, 341–350.
Graham, F. L., Bacchetti, S., McKinnon, R., Stanners, C., Cordell, B., and Goodman, H. M. (1980) In *Introduction of Macromolecules into Viable Mammalian Cells,* Eds. Baserga, R., Croce, C., and Rovera, G. (Liss, New York), Vol. 1, pp. 3–25.
Higashiyama, S., Abraham, J. A., Miller, J., Fiddes, J. C., and Klagsbrun, M. (1991) Science 251, 936–939.
Higashiyama, S., Lau, K., Besner, G. E., Abraham, J. A., and Klagsbrun, M. (1992) J. Biol. Chem. 267, 6205–6212.
Hirt, B., 1967, J Mol Biol, 26, 365–369
Hobbs, H. H., Russell, D. W., Brown, M. S., and Goldstein, J. L. (1990). Annu. Rev. Genet. 24, 133–170.
Ittelson, T. R., and Gill, D. M. (1973) Nature 242, 330–332.
Iwamoto, R., Senoh, H., Okada, Y., Uchida, T., and Mekada, E. (1991) J. Biol. Chem. 266, 20463–20469.
Jing, S., Spencer, T., Miller, K., Hopkins, C., and Trowbridge, I. S. (1990) J. Cell Biol. 110, 283–294.
Kaufman, J. F., Krangel, M. S., and Strominger, J. L. (1984) J. Biol. Chem. 259, 7230–7238.
Klein, R., Parada, L. F., Coulier, F., and Barbacid, M. (1989) EMBO J. 8, 3701–3709.
Keen, J. H., Maxfield, F. R., Hardegree, M. C., and Habig, W. H. (1982) Proc. Natl. Acad. Sci. U.S.A. 79, 2912–2916.
Kornfeld, R. and Kornfeld, S. (1980). Structure of glycoproteins and their oligosaccharide units. In *The Biochemistry of Glycoproteins and Proteoglycans.* Ed., Lennarz, W. J. New York: Plenum, pp. 1–34.
Kozak, M. (1987) Nucl. Acids Res. 15, 8125–8148.
Kyte et al., (1982) J. Mol. Biol. 157, 105–132.
Littman, D. R., Thomas, Y., Maddon, P. J., Chess, L., and Axel, R. (1985) Cell 40, 237–246.
Lobel, P., Fujimoto, K., Ye, R. D., Griffiths, G., and Kornfeld, S. (1989) Cell 57, 787–796.
Massague, J. (1990). J. Biol. Chem. 265, 21393–21396.
Margolskee, R. F., Kavathas, P., and Berg, P., 1988,Mol. Cell. Biol. 8, 2837–2847.
Matthews, L. S., and Vale, W. W. (1991) Cell 65, 973–982.
Mekada, E., and Uchida, T. (1985) J. Biol. Chem. 260, 12148–12153.
Middlebrook, J. L., and Dorland, R. B. (1977a) Can. J. Microbiol. 23, 175–182.
Middlebrook, J. L., and Dorland, R. B. (1977b) Can. J. Microbiol. 23, 183–189.
Middlebrook, J. L., Dorland, R. B., and Leppla, S. H. (1978) J. Biol. Chem. 253, 7325–7330.
Middlebrook, J. L., and Dorland, R. B. (1984) Microbiol. Rev. 48, 199–221.
Morris, R. E., Gerstein, A. S., Bonventre, P. F., and Saelinger, C. B. (1985) Infect. Immun. 50, 721–727.
Moskaug, J. O., Sandvig, K., and Olsnes, S. (1987) J. Biol. Chem. 262, 10339–10345.
Mroczkowski, B., Reich, M., Chen, K., Bell, G. I., and Cohen, S. (1989) Mol. Cell. Biol. 9, 2771–2778.
Naglich, J. G., and Eidels, L. (1990) Proc. Natl. Acad. Sci. U.S.A. 87, 7250–7254.
Nef, P., Oneyser, C., Alliod, C., Couturier, S., and Ballivet, M. (1988) EMBO J. 7, 595–601.
Pandiella, A., and Massague, J. (1991) Proc. Natl. Acad. Sci. USA 88, 1726–1730.
Pappenheimer, A. M., Jr. (1977) Ann. Rev. Biochem. 46, 69–94.
Pappenheimer, A. M., Jr., Uchida, T., and Harper, A. A. (1972) Immunochemistry 9, 891–906.
Plowman, G. D., Green, J. M., McDonald, V. L., Neubauer, M. G., Disteche, C. M., Todaro, G. J., and Shoyab, M. (1990) Mol. Cell. Biol. 10, 1969–1981.
Proia, R. L., Wray, S. K., Hart, D. A., and Eidels, L. (1980) J. Biol. Chem. 255, 12025–12033.
Proia, R. L., Eidels, L., and Hart, D.A. (1981) J. Biol. Chem. 256, 4991–4997.
Rolf, J. M., Gaudin, H. M., Tirrell, S. M., MacDonald, A. B., and Eidels, L. (1989) Proc. Natl. Acad. Sci. U.S.A. 86, 2036–2039.
Roll, J. M., Gaudin, H. M., and Eidels, L. (1990) J. Biol. Chem. 265, 7331–7337.
Ryser, H. J.-P., Mandel, R., and Ghani, F. (1991) J. Biol. Chem. 266, 18439–18442.
Sabatini, D. D., Kreibich, G., Morimoto, T., and Adesnik, M. (1982) J. Cell Biol. 92, 1–22.
Sambrook, J., Fritsch, E. F., and Maniatis, T. (1989) In *Molecular Cloning: A Laboratory Manual* (Cold Spring Harbor Lab., Cold Spring Harbor, N.Y.).
Sandvig, K., and Olsnes, S. (1980) J. Cell Biol. 87, 828–832.
Sanger, F., Nicklen, S., and Coulson, A. R. (1977) Proc. Natl. Acad. Sci. USA, 74, 5463–5467
Schild, H. O. (1957) Pharmacol. Rev. 9, 242–246.
Shoyab, M., Plowman, G. D., McDonald, V. L., Bradley, J. G., and Todaro, G. J. (1989) Science 243, 1074–1076.
Southern, E. M. (1975) J. Mol. Biol. 98, 503–517.
Squinto, , S. P., Stitt, T. N., Aldrich, T. H., Davis, S., Bianco, S. M., Radziejewski, C., Glass, D. J., Masiakowski, P., Furth, M. E., Valenzuela, D. M., DiStefano, P. S., and Yancopoulos, G. D. (1991). Cell 65, 885–893.
Stenmark, H., Olsnes, S., and Sandvig, K. (1988) J. Biol. Chem. 263, 13449–13455.
Thomsen, D. R., Stenberg, R. M., Goins, W. F., and Stinski, M. F. (1984) Proc. Natl. Acad. Sci. U.S.A. 81, 659–663.
von Heijne, G., (1986) Nucl. Acids Res. 14, 4683–4690.
Wieland, I., Bolger, G., Asouline, G., and Wigler, M. (1990) Proc. Natl. Acad. Sci. USA 87, 2720–2724.
Wong, S. T., Winchell, L. F., McCune, B. K. Earp, H. S., Teixido, J., Massague, J., Herman, B., and Lee, D. C. (1989) Cell 56, 495–506.
Wright, H. T., Marston, A. W., and Goldstein, D. J. (1984) J. Biol. Chem. 259, 1649–1654.

SEQUENCE LISTING

-continued ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 1063 BASE PAIRS
( B ) TYPE: NUCLEIC ACID
( C ) STRANDEDNESS: SINGLE
( D ) TOPOLOGY: LINEAR ( i i ) MOLECULE TYPE: DNA ( i i i ) SEQUENCE DESCRIPTION: SEQ ID NO: 1:

CTCTAAAGGC CGCTTCGAAA GTGACTGGTG CCTCGCCGCC TCCTCTCGGT GCGGGACCAT 60

GAAGCTGCTG CCGTCGGTGG TGCTGAAGCT CCTTCTGGCT GCAGTTCTTT CGGCACTGGT 120

GACTGGCGAG AGCCTGGAGC AGCTTCGGAG AGGGCTAGCT GCTGGAACCA GCAACCCGGA 180

CCCTTCCACT GGATCTACGG ACCAGCTGCT ACGCCTAGGA GGCGGCCGGG ACCGGAAAGT 240

CCGTGACTTG CAAGAGGCAG ATCTGGACCT TTTGAGAGTC ACTTTATCCT CCAAGCCACA 300

AGCACTGGCC ACACCAAGCA AGGAGGAGCA CGGGAAAAGA AAGAAGAAAG GCAAGGGACT 360

AGGGAAGAAG AGGGACCCAT GTCTTCGGAA ATACAAGGAC TTCTGCATCC ACGGAGAATG 420

CAAATATGTG AAGGAGCTCC GGGCTCCCTC CTGCATCTGC CACCCAGGTT ACCATGGAGA 480

GAGGTGTCAT GGGCTGAGCC TCCCAGTGGA AAATCGCTTA TATACCTATG ACCATACAAC 540

TATCCTGGCT GTGGTGGCCG TGGTGCTGTC CTCTGTCTGT CTGCTGGTCA TCGTGGGGCT 600

TCTCATGTTT AGGTACCATA GGAGAGGTGG TTATGATGTG GAAAACGAAG AGAAAGTGAA 660

GTTGGGCATG ACTAATTCCC ACTGAGAGAG ACTTGTGCTC AAGGAATCAG CTGGTGACTG 720

CTACCTCTGA GAAGACACAA GGTGATTTCA GACTGCAGAG GGGAAAGACG TCACATCTAG 780

CCACAAAGAC TCCTTCATCC CCAGTCGCCA TCTAGGATTG GGCCTCCCAT AATTGCTTTG 840

CCAAAATACC AGAGCCTTCA AGTGCCAAAC CGAGTATGTC TGATGGTATC TGGGTGAGAA 900

GAAAGCAAAA GCAAGGGACC TTCATGCCCT TCTGATTCCC CTCCACCAAG CCCCACTTCC 960

CCTTATAAGT TTGTTTAAGC ACTTACTTCT GGATTAGAAT GCCGGTTAAA TTCCATATGC 1020

TCCAGGATCT TTGACTGAAG AAAAAAAAAA AAAAAAAAAA AAA 1063

( 2 ) INFORMATION FOR SEQ ID NO:2:

( i ) SEQUENCE CHARACTERISTICS:
( A ) LENGTH: 208 BASE PAIRS
( B ) TYPE: AMINO ACIDS
( C ) STRANDEDNESS: SINGLE
( D ) TOPOLOGY: LINEAR ( i i ) MOLECULE TYPE: PROTEIN ( x i ) SEQUENCE DESCRIPTION: SEQ ID NO:2:

```
Met Lys Leu Leu Pro Ser Val Val Leu Lys Leu Leu Leu Ala Ala Val
1               5                   10                  15

Leu Ser Ala Leu Val Thr Gly Glu Ser Leu Glu Gln Leu Arg Arg Gly
20                  25                  30

Leu Ala Ala Gly Thr Ser Asn Pro Asp Pro Ser Thr Gly Ser Thr Asp
35                  40                  45

Gln Leu Leu Arg Leu Gly Gly Gly Arg Asp Arg Lys Val Arg Asp Leu
50                  55                  60

Gln Glu Ala Asp Leu Asp Leu Leu Arg Val Thr Leu Ser Ser Lys Pro
65                  70                  75                  80

Gln Ala Leu Ala Thr Pro Ser Lys Glu Glu His Gly Lys Arg Lys Lys
```

-continued

| | | | | | | | | | | | | | | | |
|---|---|---|---|---|---|---|---|---|---|---|---|---|---|---|---|
| 85 | | | | | 90 | | | | | 95 | | | | | |
| Lys | Gly | Lys | Gly | Leu | Gly | Lys | Lys | Arg | Asp | Pro | Cys | Leu | Arg | Lys | Tyr |
| 100 | | | | | 105 | | | | | 110 | | | | | |
| Lys | Asp | Phe | Cys | Ile | His | Gly | Glu | Cys | Lys | Tyr | Val | Lys | Glu | Leu | Arg |
| 115 | | | | | 120 | | | | | 125 | | | | | |
| Ala | Pro | Ser | Cys | Ile | Cys | His | Pro | Gly | Tyr | His | Gly | Glu | Arg | Cys | His |
| 130 | | | | | 135 | | | | | 140 | | | | | |
| Gly | Leu | Ser | Leu | Pro | Val | Glu | Asn | Arg | Leu | Tyr | Thr | Tyr | Asp | His | Thr |
| 145 | | | | | 150 | | | | | 155 | | | | | 160 |
| Thr | Ile | Leu | Ala | Val | Val | Ala | Val | Val | Leu | Ser | Ser | Val | Cys | Leu | Leu |
| 165 | | | | | 170 | | | | | 175 | | | | | |
| Val | Ile | Val | Gly | Leu | Leu | Met | Phe | Arg | Tyr | His | Arg | Arg | Gly | Gly | Tyr |
| 180 | | | | | 185 | | | | | 190 | | | | | |
| Asp | Val | Glu | Asn | Glu | Glu | Lys | Val | Lys | Leu | Gly | Met | Thr | Asn | Ser | His |
| 195 | | | | | 200 | | | | | 205 | | | | | |

What is claimed is:

1. A method for expressing a diphtheria toxin receptor in a host cell comprising:
   (a) preparing a recombinant expression vector comprising a DNA segment encoding a diphtheria toxin receptor characterized as having the amino acid sequence as set forth in SEQ ID NO:2;
   (b) transforming a eukaryotic host cell with said recombinant expression vector;
   (c) culturing the transformed host cell to express the diphtheria toxin receptor; and
   (d) selecting transformed cells that are sensitive to diphtheria toxin.

2. A method for preparing a diphtheria toxin receptor, comprising:
   (a) expressing a diphtheria toxin receptor in a recombinant host cell in accordance with claim 1;
   (b) purifying said diphtheria toxin receptor from said recombinant host cell relative to its natural state; and
   (c) contacting said diphtheria toxin receptor with diphtheria toxin to bind said toxin to said toxin receptor.

3. A recombinant eukaryotic host cell that is sensitive to diphtheria toxin by virtue of the incorporation of a recombinant DNA segment encoding a diphtheria toxin receptor, the host cell obtainable by a process comprising the steps of:
   (a) preparing diphtheria sensitive eukaryotic cells;
   (b) preparing a recombinant clone bank comprising cDNA from the diphtheria sensitive eukaryotic cells and isolating therefrom a DNA segment encoding a diphtheria toxin receptor having an amino acid sequence as set forth in SEQ ID NO:2;
   (c) introducing the DNA segment into eukaryotic host cells to produce recombinant host cells; and
   (d) selecting therefrom a recombinant cell expressing the diphtheria toxin receptor, wherein the recombinant host cell is more sensitive to diphtheria toxin than the parent cells.

* * * * *